(12) United States Patent
Burns et al.

(10) Patent No.: US 11,337,651 B2
(45) Date of Patent: May 24, 2022

(54) MEASUREMENT OF EDEMA

(71) Applicant: BRUIN BIOMETRICS, LLC, Los Angeles, CA (US)

(72) Inventors: Martin F. Burns, Los Angeles, CA (US); Sara Barrington, Thousand Oaks, CA (US); Graham O. Ross, Glen Mills, PA (US)

(73) Assignee: Bruin Biometrics, LLC, Los Angeles, CA (US)

( * ) Notice: Subject to any disclaimer, the term of this patent is extended or adjusted under 35 U.S.C. 154(b) by 1055 days.

(21) Appl. No.: 15/887,883

(22) Filed: Feb. 2, 2018

(65) Prior Publication Data
US 2018/0220961 A1 Aug. 9, 2018

Related U.S. Application Data

(60) Provisional application No. 62/521,890, filed on Jun. 19, 2017, provisional application No. 62/454,467, filed on Feb. 3, 2017.

(51) Int. Cl.
| | |
|---|---|
| *A61B 5/00* | (2006.01) |
| *A61B 5/0531* | (2021.01) |
| *A61B 5/0537* | (2021.01) |
| *G01R 27/26* | (2006.01) |

(52) U.S. Cl.
CPC .......... *A61B 5/4878* (2013.01); *A61B 5/0531* (2013.01); *A61B 5/0537* (2013.01); *A61B 5/443* (2013.01); *A61B 5/445* (2013.01); *G01R 27/2605* (2013.01)

(58) Field of Classification Search
CPC ... A61B 5/4881; A61B 5/4878; A61B 5/0531; A61B 5/0537; A61B 5/443; A61B 5/445; G01R 27/2605
See application file for complete search history.

(56) References Cited

U.S. PATENT DOCUMENTS

| | | | |
|---|---|---|---|
| 4,295,009 A | | 10/1981 | Weidler |
| 4,557,271 A | * | 12/1985 | Stoller ................. A61B 5/2415 600/547 |
| 4,857,716 A | | 8/1989 | Gombrich et al. |
| 4,860,753 A | | 8/1989 | Amerena |
| 5,073,126 A | | 12/1991 | Kikuchi et al. |
| 5,284,150 A | | 2/1994 | Butterfield et al. |

(Continued)

FOREIGN PATENT DOCUMENTS

| | | |
|---|---|---|
| CA | 2811609 | 11/2011 |
| CA | 2609842 C | 10/2016 |

(Continued)

OTHER PUBLICATIONS

Black, J. M., Brindle, C. T., & Honaker, J. S. (Jun. 30, 2015). Differential diagnosis of suspected deep tissue injury. International wound journal, 13(4), 531-539. (Year: 2015).*

(Continued)

*Primary Examiner* — Patrick Fernandes
(74) *Attorney, Agent, or Firm* — Arnold & Porter Kaye Scholer LLP

(57) ABSTRACT

The present disclosure provides apparatuses and methods for measuring sub-epidermal moisture to provide clinicians with information related to physical conditions and ailments associated with accumulation or depletion of extracellular fluid.

8 Claims, 7 Drawing Sheets

(56) References Cited

U.S. PATENT DOCUMENTS

| | | | |
|---|---|---|---|
| 5,292,341 A | 3/1994 | Snell | |
| 5,367,789 A | 11/1994 | Lamont | |
| 5,815,416 A | 9/1998 | Liebmann et al. | |
| 5,904,581 A | 5/1999 | Pope et al. | |
| 6,223,088 B1 | 4/2001 | Scharnberg et al. | |
| 6,312,263 B1 | 11/2001 | Higuchi et al. | |
| 6,330,479 B1 | 12/2001 | Stauffer | |
| 6,370,426 B1 | 4/2002 | Campbell et al. | |
| 6,434,422 B1 | 8/2002 | Tomoda et al. | |
| 6,577,700 B1 | 6/2003 | Fan et al. | |
| 6,634,045 B1 | 10/2003 | DuDonis et al. | |
| 6,738,798 B1 | 5/2004 | Ploetz et al. | |
| 6,756,793 B2 | 6/2004 | Hirono et al. | |
| 6,963,772 B2 | 11/2005 | Bloom et al. | |
| 7,079,899 B2 | 7/2006 | Petrofsky | |
| 7,315,767 B2 | 1/2008 | Caduff et al. | |
| 7,402,135 B2 | 7/2008 | Leveque et al. | |
| 7,783,344 B2 | 8/2010 | Lackey et al. | |
| 8,011,041 B2 | 9/2011 | Hann | |
| 8,060,315 B2 | 11/2011 | Brosette et al. | |
| 8,355,925 B2 | 1/2013 | Rothman et al. | |
| 8,390,583 B2 | 3/2013 | Forutanpour et al. | |
| 8,494,617 B2 | 7/2013 | Baker, Jr. et al. | |
| 8,925,392 B2 | 1/2015 | Esposito et al. | |
| 9,028,407 B1 | 5/2015 | Bennett-Guerrero | |
| 9,095,305 B2 | 8/2015 | Engler et al. | |
| 9,220,455 B2 * | 12/2015 | Sarrafzadeh | A61B 5/447 |
| 9,271,676 B2 | 3/2016 | Alanen et al. | |
| 9,398,879 B2 | 7/2016 | Sarrafzadeh et al. | |
| 9,675,289 B2 | 6/2017 | Heaton | |
| 9,763,596 B2 | 9/2017 | Tonar et al. | |
| 9,949,683 B2 | 4/2018 | Afentakis | |
| 9,980,673 B2 | 5/2018 | Sarrafzadeh et al. | |
| 10,085,643 B2 | 10/2018 | Bandic et al. | |
| 10,166,387 B2 | 1/2019 | Bergelin et al. | |
| 10,178,961 B2 | 1/2019 | Tonar et al. | |
| 10,182,740 B2 | 1/2019 | Tonar et al. | |
| 10,188,340 B2 | 1/2019 | Sarrafzadeh et al. | |
| 10,194,856 B2 | 2/2019 | Afentakis et al. | |
| 10,206,604 B2 | 2/2019 | Bergelin et al. | |
| 10,226,187 B2 | 3/2019 | Al-Ali et al. | |
| 10,278,636 B2 | 5/2019 | Wu et al. | |
| 10,285,898 B2 | 5/2019 | Douglas et al. | |
| 10,307,060 B2 | 6/2019 | Tran | |
| 10,342,482 B1 | 7/2019 | Lisy et al. | |
| 10,383,527 B2 | 8/2019 | Al-Ali | |
| 10,420,602 B2 | 9/2019 | Horton et al. | |
| 10,441,185 B2 | 10/2019 | Rogers et al. | |
| 10,448,844 B2 | 10/2019 | Al-Ali et al. | |
| 10,463,293 B2 | 11/2019 | Maharbiz et al. | |
| 10,485,447 B2 | 11/2019 | Tonar et al. | |
| 2001/0051783 A1 | 12/2001 | Edwards et al. | |
| 2002/0016535 A1 | 2/2002 | Martin et al. | |
| 2002/0070866 A1 | 6/2002 | Newham | |
| 2002/0112898 A1 | 8/2002 | Honda et al. | |
| 2002/0143262 A1 | 10/2002 | Bardy | |
| 2003/0009244 A1 | 1/2003 | Engleson et al. | |
| 2003/0036674 A1 | 2/2003 | Bouton | |
| 2003/0036713 A1 | 2/2003 | Bouton et al. | |
| 2003/0110662 A1 | 6/2003 | Gilman et al. | |
| 2003/0116447 A1 | 6/2003 | Surridge et al. | |
| 2003/0139255 A1 | 7/2003 | Lina | |
| 2004/0041029 A1 | 3/2004 | Postman et al. | |
| 2004/0046668 A1 | 3/2004 | Smith et al. | |
| 2004/0054298 A1 | 3/2004 | Masuo et al. | |
| 2004/0080325 A1 | 4/2004 | Ogura | |
| 2004/0133092 A1 | 7/2004 | Kain | |
| 2004/0171962 A1 | 9/2004 | Leveque et al. | |
| 2004/0176754 A1 | 9/2004 | Island et al. | |
| 2004/0236200 A1 | 11/2004 | Say et al. | |
| 2004/0254457 A1 | 12/2004 | Van Der Weide | |
| 2005/0027175 A1 | 2/2005 | Yang | |
| 2005/0070778 A1 | 3/2005 | Lackey et al. | |
| 2005/0086072 A1 | 4/2005 | Fox, Jr. et al. | |
| 2005/0096513 A1 | 5/2005 | Ozguz et al. | |
| 2005/0177061 A1 | 8/2005 | Alanen et al. | |
| 2005/0203435 A1 | 9/2005 | Nakada | |
| 2005/0215918 A1 | 9/2005 | Frantz et al. | |
| 2005/0245795 A1 | 11/2005 | Goode et al. | |
| 2005/0251418 A1 | 11/2005 | Fox, Jr. et al. | |
| 2006/0052678 A1 | 3/2006 | Drinan et al. | |
| 2006/0058593 A1 * | 3/2006 | Drinan | A61B 5/6807 600/301 |
| 2006/0097949 A1 | 5/2006 | Luebke et al. | |
| 2006/0206013 A1 | 9/2006 | Rothman et al. | |
| 2007/0106172 A1 | 5/2007 | Abreu | |
| 2007/0179585 A1 | 8/2007 | Chandler et al. | |
| 2007/0191273 A1 * | 8/2007 | Ambati | A61K 38/177 514/44 R |
| 2007/0213700 A1 | 9/2007 | Davison et al. | |
| 2008/0009764 A1 | 1/2008 | Davies | |
| 2008/0015894 A1 | 1/2008 | Miller et al. | |
| 2008/0048680 A1 | 2/2008 | Hargreaves et al. | |
| 2008/0259577 A1 | 10/2008 | Hu et al. | |
| 2008/0278336 A1 | 11/2008 | Ortega et al. | |
| 2009/0104797 A1 | 4/2009 | Tseng et al. | |
| 2009/0124924 A1 | 5/2009 | Eror et al. | |
| 2009/0189092 A1 | 7/2009 | Aoi et al. | |
| 2009/0285785 A1 | 11/2009 | Jimi et al. | |
| 2009/0326346 A1 | 12/2009 | Kracker et al. | |
| 2010/0017182 A1 | 1/2010 | Voros et al. | |
| 2010/0030167 A1 | 2/2010 | Thirstrup et al. | |
| 2010/0042389 A1 | 2/2010 | Farruggia et al. | |
| 2010/0113979 A1 | 5/2010 | Sarrafzadeh et al. | |
| 2010/0268111 A1 | 10/2010 | Drinan et al. | |
| 2010/0298687 A1 | 11/2010 | Yoo et al. | |
| 2010/0312233 A1 | 12/2010 | Furnish et al. | |
| 2010/0324455 A1 | 12/2010 | Rangel et al. | |
| 2010/0324611 A1 | 12/2010 | Deming et al. | |
| 2011/0046505 A1 | 2/2011 | Cornish et al. | |
| 2011/0160548 A1 | 6/2011 | Forster | |
| 2011/0184264 A1 | 7/2011 | Galasso et al. | |
| 2011/0191122 A1 | 8/2011 | Kharraz Tavakol et al. | |
| 2011/0237926 A1 * | 9/2011 | Jensen | A61B 5/0537 600/393 |
| 2011/0263950 A1 | 10/2011 | Larson et al. | |
| 2011/0301441 A1 | 12/2011 | Bandic et al. | |
| 2011/0313311 A1 | 12/2011 | Gaw | |
| 2012/0029410 A1 | 2/2012 | Koenig et al. | |
| 2012/0061257 A1 | 3/2012 | Yu et al. | |
| 2012/0078088 A1 | 3/2012 | Whitestone et al. | |
| 2012/0150011 A1 | 6/2012 | Besio | |
| 2012/0179006 A1 | 7/2012 | Jansen et al. | |
| 2012/0190989 A1 * | 7/2012 | Kaiser | A61B 5/0031 600/476 |
| 2012/0271121 A1 | 10/2012 | Della Torre et al. | |
| 2013/0041235 A1 * | 2/2013 | Rogers | A61B 5/1107 600/306 |
| 2013/0072870 A1 | 3/2013 | Heppe et al. | |
| 2013/0121544 A1 * | 5/2013 | Sarrafzadeh | A61B 5/445 382/128 |
| 2013/0123587 A1 | 5/2013 | Sarrafzadeh et al. | |
| 2013/0137951 A1 | 5/2013 | Chuang et al. | |
| 2013/0253285 A1 | 9/2013 | Bly et al. | |
| 2013/0261496 A1 | 10/2013 | Engler et al. | |
| 2013/0301255 A1 | 11/2013 | Kim et al. | |
| 2013/0310440 A1 | 11/2013 | Duskin et al. | |
| 2013/0333094 A1 | 12/2013 | Rogers et al. | |
| 2013/0338661 A1 | 12/2013 | Behnke, II | |
| 2014/0121479 A1 | 5/2014 | O'Connor et al. | |
| 2014/0142984 A1 | 5/2014 | Wright et al. | |
| 2014/0288397 A1 | 6/2014 | Sarrafzadeh et al. | |
| 2014/0200486 A1 | 7/2014 | Bechtel et al. | |
| 2014/0273025 A1 | 9/2014 | Hurskainen et al. | |
| 2014/0275823 A1 | 9/2014 | Lane et al. | |
| 2014/0298928 A1 | 10/2014 | Duesterhoft et al. | |
| 2014/0316297 A1 | 10/2014 | McCaughan et al. | |
| 2014/0318699 A1 | 10/2014 | Longinotti-Buitoni et al. | |
| 2015/0002168 A1 | 1/2015 | Kao et al. | |
| 2015/0009168 A1 | 1/2015 | Levesque et al. | |
| 2015/0094548 A1 | 4/2015 | Sabatini et al. | |
| 2015/0186607 A1 | 7/2015 | Gileijnse et al. | |
| 2015/0230863 A1 | 8/2015 | Youngquist et al. | |
| 2015/0363567 A1 | 12/2015 | Pettus | |

(56) References Cited

U.S. PATENT DOCUMENTS

| | | |
|---|---|---|
| 2015/0366499 A1 | 12/2015 | Sarrafzadeh et al. |
| 2015/0371522 A1 | 12/2015 | Mravyan et al. |
| 2016/0015962 A1 | 1/2016 | Shokoueinejad Maragheh et al. |
| 2016/0038055 A1 | 2/2016 | Wheeler et al. |
| 2016/0072308 A1 | 3/2016 | Nyberg et al. |
| 2016/0100790 A1 | 4/2016 | Cantu et al. |
| 2016/0101282 A1 | 4/2016 | Bergelin et al. |
| 2016/0174871 A1 | 6/2016 | Sarrafzadeh et al. |
| 2016/0220172 A1 | 8/2016 | Sarrafzadeh et al. |
| 2016/0270672 A1 | 9/2016 | Chen et al. |
| 2016/0270968 A1 | 9/2016 | Stanford et al. |
| 2016/0278692 A1 | 9/2016 | Larson et al. |
| 2016/0296268 A1 | 10/2016 | Gee et al. |
| 2016/0310034 A1* | 10/2016 | Tonar .................. A61B 5/4875 |
| 2016/0338591 A1* | 11/2016 | Lachenbruch ....... A61B 5/7405 |
| 2017/0007153 A1 | 1/2017 | Tonar et al. |
| 2017/0014044 A1 | 1/2017 | Tonar et al. |
| 2017/0014045 A1 | 1/2017 | Tonar et al. |
| 2017/0156658 A1 | 6/2017 | Maharbiz et al. |
| 2017/0172489 A1* | 6/2017 | Afentakis .............. A61B 5/447 |
| 2017/0188841 A1 | 7/2017 | Ma et al. |
| 2017/0238849 A1 | 8/2017 | Chapman et al. |
| 2017/0255812 A1 | 9/2017 | Kwon |
| 2017/0311807 A1 | 11/2017 | Fu et al. |
| 2017/0319073 A1 | 11/2017 | DiMaio et al. |
| 2018/0020058 A1 | 1/2018 | Martines et al. |
| 2018/0045725 A1 | 2/2018 | Yoo et al. |
| 2018/0220924 A1 | 8/2018 | Burns et al. |
| 2018/0220953 A1 | 8/2018 | Burns et al. |
| 2018/0220954 A1 | 8/2018 | Burns et al. |
| 2018/0360344 A1 | 12/2018 | Burns et al. |
| 2019/0000352 A1 | 1/2019 | Everett et al. |
| 2019/0038133 A1 | 2/2019 | Tran |
| 2019/0060602 A1 | 2/2019 | Tran et al. |
| 2019/0104981 A1 | 4/2019 | Sarrafzadeh et al. |
| 2019/0104982 A1 | 4/2019 | Dunn et al. |
| 2019/0134396 A1* | 5/2019 | Toth ......................... A61N 1/08 |
| 2019/0142333 A1 | 5/2019 | Burns et al. |
| 2019/0147990 A1 | 5/2019 | Burns et al. |
| 2019/0148901 A1 | 5/2019 | Komoto |
| 2019/0150882 A1 | 5/2019 | Maharbiz et al. |
| 2019/0175098 A1 | 6/2019 | Burns et al. |
| 2019/0192066 A1 | 6/2019 | Schoess et al. |
| 2019/0246972 A1 | 8/2019 | Burns et al. |
| 2019/0282436 A1 | 9/2019 | Douglas et al. |
| 2019/0290189 A1 | 9/2019 | Sarrafzadeh et al. |
| 2019/0307360 A1 | 10/2019 | Tonar et al. |
| 2019/0307405 A1 | 10/2019 | Terry et al. |
| 2020/0069240 A1 | 3/2020 | Burns |
| 2020/0069241 A1 | 3/2020 | Burns |
| 2020/0069242 A1 | 3/2020 | Burns et al. |
| 2020/0077892 A1 | 3/2020 | Tran |
| 2020/0078499 A1 | 3/2020 | Gadde et al. |
| 2020/0093395 A1 | 3/2020 | Tonar et al. |
| 2020/0100723 A1 | 4/2020 | Burns |
| 2020/0113488 A1 | 4/2020 | Al-Ali et al. |
| 2020/0127398 A1 | 4/2020 | Burns et al. |
| 2020/0296821 A1 | 9/2020 | Trublowski et al. |
| 2020/0297244 A1 | 9/2020 | Brownhill et al. |
| 2020/0297255 A1 | 9/2020 | Martinez et al. |

FOREIGN PATENT DOCUMENTS

| | | |
|---|---|---|
| CN | 204119175 U | 1/2015 |
| CN | 104567657 A | 4/2015 |
| CN | 208111467 U | 11/2018 |
| DE | 102012011212 A1 | 1/2012 |
| EP | 1080687 A1 | 3/2001 |
| EP | 1372475 B1 | 1/2004 |
| EP | 1569553 A1 | 9/2005 |
| EP | 3092946 A1 | 11/2016 |
| EP | 3280488 B1 | 12/2018 |
| GB | 2584808 A | 12/2020 |
| JP | 2003-169788 A | 6/2003 |
| JP | 2003-290166 A | 10/2003 |
| JP | 2005-52227 | 3/2005 |
| JP | 4418419 | 2/2010 |
| JP | 2013-528428 | 7/2013 |
| JP | 2013-198639 A | 10/2013 |
| JP | 2015-509028 | 3/2015 |
| JP | 2016-519969 | 7/2016 |
| JP | 2016-527943 A | 9/2016 |
| KR | 10-2014-0058445 | 5/2014 |
| WO | 96/10951 A1 | 4/1996 |
| WO | 2006/029035 A1 | 3/2000 |
| WO | 2001/054580 A1 | 8/2001 |
| WO | 2002/080770 A1 | 10/2002 |
| WO | 2004/105602 A1 | 12/2004 |
| WO | 2007/098762 A1 | 9/2007 |
| WO | 2009/144615 A1 | 12/2009 |
| WO | 2010/060102 A2 | 5/2010 |
| WO | 2011/022418 A2 | 2/2011 |
| WO | 2011/080080 A1 | 7/2011 |
| WO | 2011/080262 A1 | 7/2011 |
| WO | 2011/143071 A2 | 11/2011 |
| WO | 2013/116242 A2 | 8/2013 |
| WO | 2014/186894 A1 | 11/2014 |
| WO | 2015/003015 A2 | 1/2015 |
| WO | 2015/077838 A1 | 6/2015 |
| WO | 2015/168720 A1 | 11/2015 |
| WO | 2015/169911 A1 | 11/2015 |
| WO | 2015/195720 A1 | 12/2015 |
| WO | 2016/172263 A1 | 10/2016 |
| WO | 2016/172264 A1 | 10/2016 |
| WO | 2017/032393 A1 | 3/2017 |
| WO | 2017/214188 A1 | 12/2017 |
| WO | 2018/071715 A1 | 4/2018 |
| WO | 2018/077560 A1 | 5/2018 |
| WO | 2018/115461 A1 | 6/2018 |
| WO | 2018/144938 | 8/2018 |
| WO | 2018/144941 | 8/2018 |
| WO | 2018/144943 | 8/2018 |
| WO | 2018/144946 | 8/2018 |
| WO | 2018/189265 A1 | 10/2018 |
| WO | 2018/209100 A1 | 11/2018 |
| WO | 2018/234443 A1 | 12/2018 |
| WO | 2018/236739 | 12/2018 |
| WO | 2019/020551 A1 | 1/2019 |
| WO | 2019/030384 A2 | 2/2019 |
| WO | 2019/048624 A1 | 3/2019 |
| WO | 2019/048626 A1 | 3/2019 |
| WO | 2019/048638 A1 | 3/2019 |
| WO | 2019/072531 A1 | 4/2019 |
| WO | 2019/073389 A1 | 4/2019 |
| WO | 2019/076967 A2 | 4/2019 |
| WO | 2019/096828 A1 | 5/2019 |
| WO | 2019/099810 | 5/2019 |
| WO | 2019/099812 A1 | 5/2019 |
| WO | 2019/113481 | 6/2019 |
| WO | 2018/162272 A1 | 8/2019 |
| WO | 2019/157290 | 8/2019 |
| WO | 2020/014779 A1 | 1/2020 |
| WO | 2020/043806 A1 | 3/2020 |
| WO | 2020/053290 A1 | 3/2020 |
| WO | 2020/077100 A1 | 4/2020 |
| WO | 2020/187643 A1 | 9/2020 |
| WO | 2020/187851 A1 | 9/2020 |
| WO | 2020/234429 A2 | 11/2020 |

OTHER PUBLICATIONS

Moore, Z., Patton, D., Rhodes, S. L., & O'Connor, T. (Apr. 29, 2016). Subepidermal moisture (SEM) and bioimpedance: a literature review of a novel method for early detection of pressure-induced tissue damage (pressure ulcers). International wound journal, 14(2), 331-337. (Year: 2016).*

International Search Report dated Sep. 10, 2018, issued in International Patent Application No. PCT/US2018/038055.

International Search Report dated Jan. 29, 2019, issued in International Patent Application No. PCT/US2018/061494.

International Search Report dated Feb. 5, 2019, issued in International Patent Application No. PCT/US2018/064527.

(56) References Cited

OTHER PUBLICATIONS

International Search Report dated Feb. 11, 2019, issued in International Patent Application No. PCT/US2018/061497.
Bergstrom et al., "Pressure Ulcers in Adults: Prediction and Prevention," *Clinical Practice Guideline—Quick Reference Guide for Clinicians*, 117 (1992).
Alanen, "Measurement of Hydration in the Stratum Corneum with the MoistureMeter and Comparison with the Corneometer," *Skin Research and Technology*, 10:32-37 (2004).
Alberts et al., "The Extracellular Matrix of Animals," *Molecular Biology of the Cell*, 4th ed., pp. 1065-1127 (2002).
Allman et al., "Pressure Ulcer Risk Factors Among Hospitalized Patiens with Activity Limitation," *JAMA*, 273:865-870 (1995).
Anonymous, "Recommended Practices for Positioning the Patient in the Perioperative Practice Setting," in *Perioperative Standards, Recommended Practices, and Guidelines*, AORN, Inc., 525-548 (2006).
Arao et al., "Morphological Characteristics of the Dermal Papillae In the Development of Pressure Sores," *World Wide Wounds*, (1999).
Australian Intellectual Property Office, Office Action dated May 1, 2014 for corresponding Australian patent application No. 2011253253 (pp. 1-10) and pending claims (pp. 11-15) pp. 1-15.
Australian Patent Office, Office Action dated Jun. 1, 2015, for corresponding Australian Patent Application No. 2011253253 (pp. 1-4) and claims (pp. 5-10) pp. 1-10.
Bader et al., "Effect of Externally Applied Skin Surface Forces on Tissue Vasculature," *Archives of Physical Medicine and Rehabilitation*, 67(11):807-11 (1986).
Barnes, "Moisture Meters for Use on Thin Lumber and Veneers," *Moisture Register Co.*, 1-5 (1956)
Bates-Jensen et al., "Subepidermal Moisture Predicts Erythema and Stage 1 Pressure Ulcers in Nursing Home Residents: A Pilot Study," *Journal of the American Geriatric Society*, 55:1199-1205 (2007).
Bates-Jensen et al., "Subepidermal moisture differentiates erythema and stage 1 pressure ulcers in nursing home residents," *Wound Repair Regeneration*, 16:189-197 (2008).
Bates-Jensen et al., "Subepidermal Moisture Is Associated With Early Pressure Ulcer Damage in Nursing Home Residents With Dark Skin Tones; Pilot Findings," *Journal of Wound Ostomy and Continence Nursing*, 36(3):277-284 (2009).
Bergstrand et al., "Pressure-induced Vasodilation and Reactive Hyperemia at Different Depths in Sacral Tissue Under Clinically Relevant Conditions," *Microcirculation*, 21:761-771 (2014).
Brem et al. "High cost of stage IV pressure ulcers," *American Journal of Surgery*, 200:473-477 (2010).
Brienza et al., "Friction-Induced Skin Injuries—Are They Pressure Ulcers?," *Journal of Wound Ostomy and Continence Nursing*, 42(1):62-64 (2015).
Carmo-Araujo et al., "Ischaemia and reperfusion effects on skeletal muscle tissue: morphological and histochemical studies," *International Journal of Experimental Pathology*, 88:147-154 (2007).
Ceelen et al., "Compression-induced damage and internal tissue strains are related," *Journal of Biomechanics*, 41:3399-3404 (2008).
Ching et al., "Tissue electrical properties monitoring for the prevention of pressure sore," *Prosthetics and Orthotics International*, 35(4):386-394 (2011).
Clendenin et al., "Inter-operator and inter-device agreement and reliability of the SEM Scanner," *Journal of Tissue Viability*, 24(1):17-23 (2015).
De Lorenzo et al., "Predicting body cell mass with bioimpedance by using theoretical methods: a technological review," *Journal of Applied Physiology*, 82(5):1542-1558 (1997).
Demarre et al., "The cost of pressure ulcer prevention and treatment in hospitals and nursing homes in Flanders: A cost-of-illness study," *International Journal of Nursing Studies*, 1-14 (2015).
Dodde et al., "Bioimpedance of soft tissue under compression," *Physiology Measurement*, 33(6): 1095-1109 (2012)

DuPont, "General Specifications for Kapton Polyimide Film," Retrieved from Dupont: http://www2.dupont.com/Kapton/en_US/assets/downloads/pdf/Gen_Specs.pdf, pp. 1-7 (2012).
Dupont, "Pyralux® FR Coverlay, Bondply & Sheet Adhesive," webpage, Retrieved from: www2.dupont.com/Pyralux/en_US/products/adhesives_films/FR/FR_films_html pp. 1-2 (2012).
Dupont, "Pyralux® FR Copper-clad Laminate," webpage, Retrieved from: www2.dupont.com/Pyraluxlen_US/productsllaminate/FR/pyralux_fr.html, pp. 1-2 (2012).
Eberlein-Gonska et al., "The Incidence and Determinants of Decubitus Ulcers in Hospital Care: An Analysis of Routine Quality Management Data at a University Hospital," *Deutsches Arzteblatt International*, 110(33-34):550-556 (2013).
European Patent Office, ESSR issued on Aug. 22, 2014 for corresponding European Patent Application No. 117811061.4 (pp. 1-7) and pending claims (pp. 3-10) pp. 1-10.
European Patent Office, Office Action dated Jul. 13, 2015, for corresponding European Patent Application No. 11781061.4 (pp. 1-5) and claims (pp. 6-9) pp. 1-9.
Extended European Search Report dated Aug. 19, 2016, in European Application No. 16169670.
Extended European Search Report dated Sep. 19, 2016, in European Patent Application No. 16166483.4.
Extended European Search Report dated Mar. 13, 2017, in European Patent Application No. 16196899.5.
Gabriel, "Compilation of the Dielectric Properties of Body Tissues at Rf and Microwave Frequencies Report," *Occupational and Environmental Health Directorate*, (1996).
Gabriel et al., "The dielectric properties of biological tissues: II. Measurements in the frequency range 10 Hz to 20 GHz," *Physics in Medicine and Biology*, 41:2251-69 (1996).
Gardiner et al., "Incidence of hospital-acquired pressure ulcers—a population-based cohort study," *International Wound Journal*, 11(6):696-700 (2014)
Gershon et al., "SEM Scanner Readings to Assess Pressure Induced Tissue Damage," Proceedings of the 17th Annual European Pressure Ulcer Advisory Panel (EPUAP) meeting, Stockholm, Sweden (2014).
Gonzalez-Correa et al., "Electrical bioimpedance readings increase with higher pressure applied to the measuring probe," *Physiology Measurement*, 26:S39-S47 (2005).
Guihan et al., "Assessing the feasibility of subepidermal moisture to predict erythema and stage 1 pressure ulcers in persons with spinal cord injury: A pilot study," *Journal of Spinal Cord Medicine*, 35(1):46-52 (2012).
Harrow, "Subepidermal moisture surrounding pressure ulcers in persons with a spinal cord injury: A pilot study," *Journal of Spinal Cord Medicine*, 37(6):719-728 (2014).
Houwing et al., "Pressure-induced skin lesions in pigs: reperfusion injury and the effects of vitamin E," *Journal of Wound Care*, 9(1):36-40 (2000).
Huang et al., "A device for skin moisture and environment humidity detection," *Sensors and Actuators B: Chemical*, 206-212 (2008).
International Search Report dated Apr. 12, 2018, issued in International Patent Application No. PCT/US2018/016731.
International Search Report dated Apr. 12, 2018, issued in International Patent Application No. PCT/US2018/016738.
International Search Report dated Apr. 26, 2018, issued in International Patent Application No. PCT/US2018/016741.
International Search Report and Written Opinion dated Feb. 9, 2012 for International Patent Application No. PCT/US2011/035618.
International Search Report and Written Opinion dated Jul. 22, 2016, for International Patent Application No. PCT/US2016/28515.
International Search Report and Written Opinion dated Jul. 26, 2016, for International Patent Application No. PCT/US2016/28516.
Jan et al., "Local cooling reduces skin ischemia under surface pressure in rats: an assessment by wavelet analysis of laser Doppler blood flow oscillations," *Physiology Measurement*, 33(10): 1733-1745 (2012).
Jaskowski, "Evaluation of the Healing Process of Skin Wounds by Means of Skin Absolute Value of Electrical Impedance," *Dermatol. Mon.schr.*, 172(4):223-228 (1986).

(56) References Cited

OTHER PUBLICATIONS

Jiang et al., "Expression of cytokines, growth factors and apoptosis-related signal molecules in chronic pressure ulcer wounds healing," *Spinal Cord,* 52(2):145-151 (2014).
Jiang et al., "Ischemia-Reperfusion Injury-Induced Histological Changes Affecting Early Stage Pressure Ulcer Development in a Rat model," *Ostomy Wound Management,* 57:55-60 (2011).
Jiricka et al., "Pressure Ulcer Risk factors in an ICU Population," *American Journal of Critical Care,* 4:361-367 (1995).
Kanai et al., "Electrical measurement of fluid distribution in legs and arms," *Medical Progress through Technology Journal,* 12:159-170 (1987).
Kasyua et al., "Potential application of in vivo imaging of impaired lymphatic duct to evaluate the severity of pressure ulcer in mouse model," *Scientific Reports,* 4:4173 (2014).
Lee, "CapSense Best Practices," *Application Note 2394,* 1-10 (2007).
Loerakker et al., "The effects of deformation, ischemia, and reperfusion on the development of muscle damage during prolonged loading," *Journal of Applied Physiology,* 111(4): 1168-1177 (2011).
Loerakker et al., "Temporal Effects of Mechanical Loading on Defoi mation-induced Damage in Skeletal Muscle Tissue," *Annual Review of Biomedical Engineering,* 38(8):2577-2587 (2010).
Lyder et al., "Quality of Care for Hospitalized Medicare Patients at Risk for Pressure Ulcers," *Archives of Internal Medicine,* 161:1549-1554 (2001).
Martinsen, "Bioimpedance and Bioelectricity Basics," *Elsevier Academic Press,* Chapters 1 and 10 (2015).
Mathiesen et al., "Are labour-intensive efforts to prevent pressure ulcers cost-effective?" *Journal of Medicinal Economics,* 16(10):1238-1245 (2013).
Matthie et al., "Analytic assessment of the various bioimpedance methods used to estimate body water," *Journal of Applied Physiology,* 84(5): 1801-1816 (1998)
Miller et al., "Lymphatic Clearance during Compressive Loading," *Lymphology,* 14(4): 161-166 (1981).
Moore et al., "A randomised controlled clinical trial of repositioning, using the 30° tilt, for the prevention of pressure ulcers," *Journal of Clinical Nursing,* 20:2633-2644 (2011).
Moore et al., "Pressure ulcer prevalence and prevention practices in care of the older person in the Republic of Ireland," *Journal of Clinical Nursing,* 21:362-371 (2012).
Moore et al., "A review of PU prevalence and incidence across Scandinavia, Iceland and Ireland (Part I)", *Journal of Wound Care,* 22(7):361-362, 364-368 (2013).
Mulasi, "Bioimpedance at the Bedside: Current Applications, Limitations, and Opportunities," *Nutritional Clinical Practice,* 30(2): 180-193 (2015).
National Pressure Ulcer Advisory Panel et al., "Prevention and Treatment of Pressure Ulcers: Clinical Practice Guideline," *Cambridge Media,* (2014).
Nixon et al., "Pathology, diagnosis, and classification of pressure ulcers: comparing clinical and imaging techniques," *Wound Repair and Regeneration,* 13(4):365-372 (2005).
Nuutinen et al., "Validation of a new dielectric device to asses changes of tissue water in skin and subcutaneous fat," *Physiological Measurement,* 25:447-454 (2004).
O'Goshi, "Skin conductance; validation of Skicon-200EX compared to the original model, Skicon-100," *Skin Research and Technology,* 13:13-18 (2007).
Oomens et al., "Pressure Induced Deep Tissue Injury Explained," *Annual Review of Biomedical Engineering,* 43(2):297-305 (2015).
Scallan et al., "Chapter 4: Pathophysiology of Edema Formation," *Capillary Fluid Exchange: Regulation, Functions, and Pathology,* 47-61 (2010).
Schultz et al., "Extracellular matrix: review of its role in acute and chronic wounds," *World Wide Wounds,* 1-20 (2005).
Schwan, "Electrical properties of tissues and cells," *Advances in Biology and Medical Physics,* 15:148-199 (1957)

Sener et al., "Pressure ulcer-induced oxidative organ injury is ameliorated by beta-glucan treatment in rats," *International Immunopharmacology,* 6(5):724-732 (2006).
Sewchuck et al., "Prevention and Early Detection of Pressure Ulcers in Patients Undergoing Cardiac Surgery," *AORN Journal,* 84(1):75-96 (2006).
Sprigle et al., "Analysis of Localized Erythema Using Clinical Indicators and Spectroscopy," *Ostomy Wound Management,* 49:42-52 (2003).
Stekelenburg et al., "Deep Tissue Injury: How Deep is Our Understanding?" *Archives of Physical Medicine Rehabilitation,* 89(7): 1410-1413 (2008).
Stekelenburg et al., "Role of ischemia and deformation in the onset of compression-induced deep tissue injury: MRI-based studies in a rat model," *Journal of Applied Physiology,* 102:2002-2011 (2007).
Swisher et al., "Impedance sensing device enables early detection of pressure ulcers in vivo," *Nature Communications,* 6:6575-6584 (2015).
Thomas et al., "Hospital-Acquired Pressure Ulcers and Risk of Death," *Journal of the American Geriatrics Society,* 44:1435-1440 (1996).
Valentinuzzi et al., "Bioelectrical Impedance Techmques in Medicine. Part II: Monitoring of Physiological Events by Impedance," *Critical Reviews in Biomedical Engineering,* 24(4-6):353-466 (1996).
Vangilder et al., "Results of Nine International Pressure Ulcer Prevalence Surveys: 1989 to 2005," *Ostomy Wound Management,* 54(2):40-54 (2008).
Wagner et al., "Bioelectrical Impedance as a Discriminator of Pressure Ulcer Risk," *Advances in Wound Care,* 9(2):30-37 (1996).
Wang, "Biomedical System for Monitoring Pressure Ulcer Development," UCLA Electronic Theses and Dissertations, California, USA, pp. 1-123 (2013).
Watanabe et al, "CT analysis of the use of the electrical impedance technique to estimate local oedema in the extremities in patients with lymphatic obstruction," *Medical and Biological Engineering and Computing,* 36(1):60-65 (1998)
Weiss, "Tissue destruction by neutrophils," *The New England Journal of Medicine,* 320(6):365-76 (1989)
International Search Report dated May 29, 2019, issued in International Patent Application No. PCT/US2019/017226.
International Search Report dated Jul. 12, 2018, issued in International Patent Application No. PCT/US2018/016736.
Black et al., "Differential Diagnosis of Suspected Deep Tissue Injury," *International Wound Journal,* 13(4):531-539 (2015).
Brem et al., "Protocol for the Successful Treatment of Pressure Ulcers," *The American Journal of Surgery,* 188 (Suppl. to Jul. 2004):9S-17S (2004).
Extended European Search Report dated Oct. 25, 2019, in European Patent Application No. 19186393.5.
Extended European Search Report dated Nov. 19, 2019, in European Patent Application No. 19190000.0.
Extended European Search Report dated Feb. 6, 2020, in European Patent Application No. 18748733.5.
Extended European Search Report dated Feb. 10, 2020, in European Patent Application No. 18748025.6.
Extended European Search Report dated Feb. 10, 2020, in European Patent Application No. 18748512.3.
Extended European Search Report dated Jun. 24, 2020, in European Patent Application No. 18747707.0.
Ford, "Hospice Wins Award for Innovation in Pressure Ulcer Prevention," *Nursing Times,* downloaded and printed on Apr. 18, 2020, from https://www.nursingtimes.net/news/research-and-innovation/hospice-wins-award-for-innovation-in-pressure-ulcer-prevention-30-11-2018/ (2018).
Great Britain Search Report dated Apr. 27, 2020, in Great Britain Patent Application No. GB2002889.0.
International Search Report dated Mar. 9, 2020, issued in International Patent Application No. PCT/US2019/055655.
International Search Report dated Dec. 8, 2020, issued in International Patent Application PCT/US2020/051134.

(56) References Cited

OTHER PUBLICATIONS

Liu et al., "A Systematic Review of Electrical Stimulation for Pressure Ulcer Prevention and Treatment in People with Spinal Cord Injuries," *The Journal of Spinal Cord Medicine,* 37(6):703-718 (2014).

Moore et al., "Subepidermal Moisture (SEM) and Bioimpedance: A Literature Review of a Novel Method for Early Detection of Pressure-Induced Tissue Damage (Pressure Ulcers)," *International Wound Journal,* 14(2):331-337 (2016).

Moore et al., "SEM Scanner Made Easy," *Wounds International,* pp. 1-6, available at www.woundsinternational.com (2018).

Oliveira, "The Accuracy of Ultrasound, Thermography, Photography and Sub-Epidermal Moisture as a Predictor of Pressure Ulcer Presence—a Systematic Review," RCSI, School of Nursing thesis (2015).

Rotaru et al., "Friction between Human Skin and Medical Textiles for Decubitus Prevention," *Tribology International,* 65:91-96 (2013)

Seibert et al., "Technical Expert Panel Summary Report: Refinement of a Cross-Setting Pressure Ulcer/Injury Quality Measure for Skilled Nursing Facilities, Inpatient Rehabilitation Facilities, Long-Term Care Hospitals, and Home Health Agencies," RTI International Abt Associates, CMS Contract No. HHSM-500-2013-130151, 49 pp. (Aug. 2019)

Supplementary Partial European Search Report dated Jan. 27, 2020, in European Application No. 18747707.

Thomas, "Prevention and Treatment of Pressure Ulcers," *J. Am. Med. Dir. Assoc.,* 7:46-59 (2006).

Truong et al., "Pressure Ulcer Prevention in the Hospital Setting Using Silicone Foam Dressings," *Cureus,* 8(8):e730, pp. 1-6 (2016).

Tur et al., "Topical Hydrogen Peroxide Treatment of Ischemic Ulcers in the Guinea Pig: Blood Recruitment in Multiple Skin Sites," *J. Am. Acad. Dermatol.,* 33:217-221 (1995).

Vowden et al., "Diabetic Foot Ulcer or Pressure Ulcer? That Is the Question," *The Diabetic Foot Journal,* 18:62-66 (2015).

Wang et al., "A Wireless Biomedical Instrument for Evidence-Based Tissue Wound Characterization," *Wireless Health,* pp. 222-223 (2010).

Zanibbi, "Pattern Recognition: An Overview," downloaded from https://www.cs.rit.edu/~rlaz/prec20092/slides/Overview.pdf, 30 pp. (2010).

Bates-Jensen et al., "Subepidermal Moisture Detection of Pressure Induced Tissue Damage on the Trunk: The Pressure Ulcer Detection Study Outcomes," *Wound Repair and Regeneration,* 25:502-511 (2017).

Great Britain Search Report dated Jun. 28, 2021, in Great Britain Patent Application No. GB2106848.1.

Hou, "Section IV. Osteofascial Compartment Syndrome," *Limbs Trauma,* 7:215-217 (2016).

International Search Report dated Aug. 17, 2021, issued in International Patent Application PCT/US2021/023818.

Saxena, *The Pocket Doctor: Obstetrics & Gynecology,* pp. 76-77 (2017)

Supplementary European Search Report dated Jul. 13, 2021, in European Patent Application No. 18887039.

Supplementary European Search Report dated Oct. 1, 2021, in European Patent Application No. 19751130.

Yang, *Handbook of Practical Burn Surgery,* p. 48 (2008).

Extended European Search Report dated Mar. 17, 2022, in European Patent Application No. 19838240.0.

Great Britain Search Report dated Feb. 9, 2022, in Great Britain Patent Application No. GB2118088.0.

Great Britain Search Report dated Feb. 14, 2022, in Great Britain Patent Application No. GB2118092.2.

\* cited by examiner

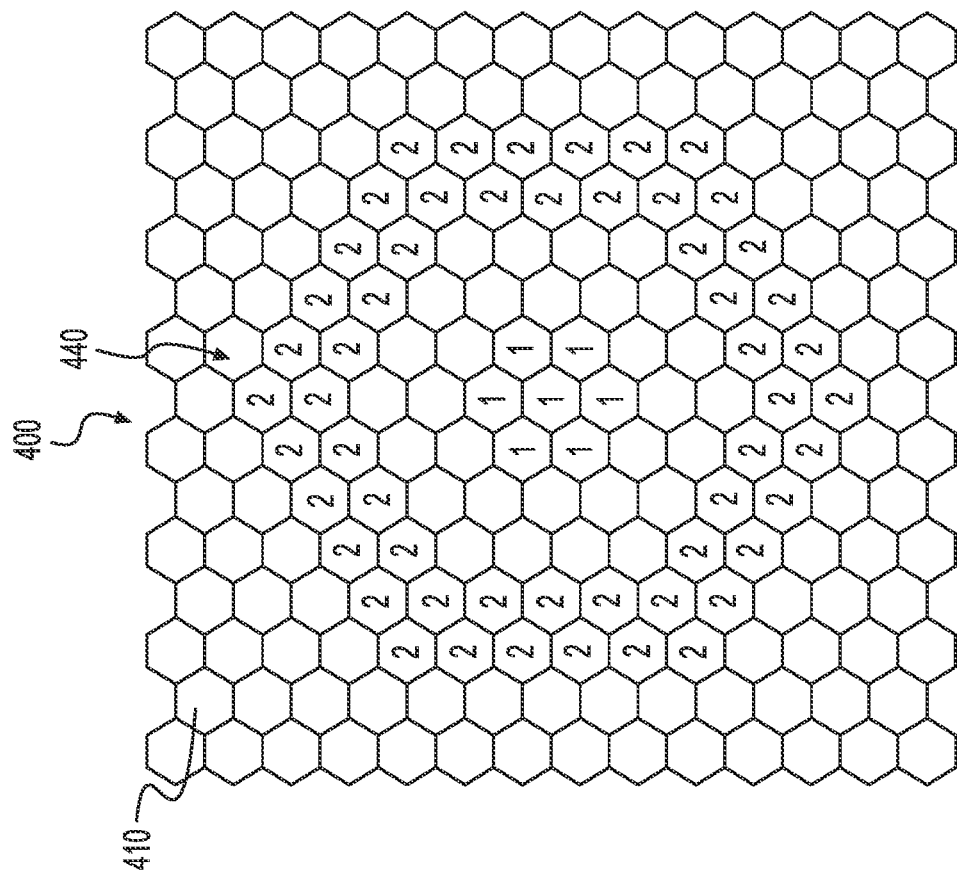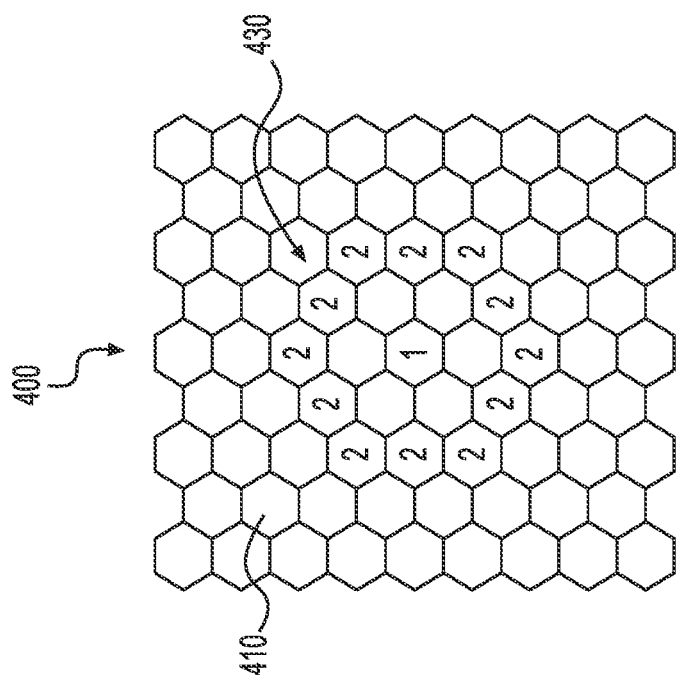

MEASUREMENT OF EDEMA

CROSS-REFERENCE TO RELATED APPLICATIONS

This application claims the benefit of priority of U.S. Provisional Application 62/454,467 filed Feb. 3, 2017, and U.S. Provisional Application 62/521,890 filed Jun. 19, 2017, each of which is herein incorporated by reference in its entirety.

FIELD

The present disclosure provides apparatus and methods for measuring sub-epidermal moisture (SEM) in patients as an indication of tissue damage associated with elevated or diminished levels of moisture in the tissue.

DESCRIPTION OF THE RELATED ART

Many physical conditions and diseases cause the tissue structure of a patient to degrade, allowing fluid to leak into the interstitial spaces between cells, causing swelling known as "edema." Other conditions reduce the amount of extra-cellular fluid (ECF) in certain tissues.

Preeclampsia is a potentially life-threatening condition that affects about 5 percent of pregnant women. It ranges in impact from mild to severe, in which case it can cause serious or even life-threatening problems. One effect of preeclampsia is for blood vessels to constrict thereby causing high blood cause changes in capillaries that allow fluid to "leak" into the surrounding tissue, thereby causing edema. This swelling may happen in the face, hands, or feet or ankles.

Dehydration may cause a reduced level of moisture in the body, which may result in low blood volume that reduces the amount oxygen delivered to tissue. Local dehydration at the surface of a wound, which may be caused by general dehydration of a patient or by local damage, may slow cellular migration and delay the healing process.

Another condition associated with edema is "compartment syndrome." Groups of organs or muscles are organized into areas called "compartments." Strong webs of connective tissue called "fascia" form the walls of these compartments. After an injury, blood or fluid may accumulate in the compartment. The fascia cannot easily expand and therefore the pressure in the compartment increases, preventing adequate blood flow to tissues inside the compartment that may result in tissue damage. When this condition occurs in a limb, such as a lower leg, the increase in pressure may cause swelling of the affected limb.

SUMMARY

In an aspect, the present disclosure provides for, and includes, an apparatus for assessing preeclampsia, the apparatus comprising: a sensor comprising at least one first electrode and at least one second electrode, where the sensor is configured to be placed against a patient's skin; a circuit electronically coupled to the first and second electrodes and configured to measure an electrical property between the first and second electrodes and provide information regarding the electrical property; a processor electronically coupled to the circuit; and a non-transitory computer-readable medium electronically coupled to the processor and comprising instructions stored thereon that, when executed on the processor, perform the steps of: receiving the information from the circuit, converting the information into a first sub-epidermal moisture (SEM) value, and determining a difference between the first SEM value and a reference value, where the magnitude of the difference exceeding the reference value is indicative of preeclampsia.

An aspect of the present disclosure provides for, and includes, an apparatus for assessing hypovolemia, the apparatus comprising: a sensor comprising at least one first electrode and at least one second electrode, where the sensor is configured to be placed against a patient's skin; a circuit electronically coupled to the first and second electrodes and configured to measure an electrical property between the first and second electrodes and provide information regarding the electrical property; a processor electronically coupled to the circuit, and a non-transitory computer-readable medium electronically coupled to the processor and comprising instructions stored thereon that, when executed on the processor, perform the steps of: receiving the information from the circuit, converting the information into a first SEM value, and determining a difference between the first SEM value and a reference value, where the magnitude of the difference lesser than the reference value is indicative of hypovolemia.

In one aspect, the present disclosure provides for, and includes, a method for detecting preeclampsia at a first location of a patient's skin, the method comprising: obtaining a sub-epidermal moisture (SEM) value at the first location; and determining that the SEM value is greater than a reference value to indicate preeclampsia.

In an aspect, the present disclosure provides for, and includes, a method for detecting hypovolemia at a first location of a patient's skin, the method comprising: obtaining a sub-epidermal moisture (SEM) value at the first location; and determining that the SEM value is lesser than a reference value to indicate hypovolemia.

An aspect of the present disclosure provides for, and includes, an apparatus for assessing compartment syndrome, the apparatus comprising: a sensor comprising at least one first electrode and at least one second electrode, where the sensor is configured to be placed against a patient's skin, a circuit electronically coupled to the first and second electrodes and configured to measure an electrical property between the first and second electrodes and provide information regarding the electrical property, a processor electronically coupled to the circuit, and a non-transitory computer-readable medium electronically coupled to the processor and comprising instructions stored thereon that, when executed on the processor, perform the steps of: receiving information from the circuit, converting the information into a first sub-epidermal moisture (SEM) value, and determining a difference between the first SEM value and a reference value, where the magnitude of the difference exceeding a predetermined amount is indicative of compartment syndrome.

In an aspect, the present disclosure provides for, and includes, a method for detecting compartment syndrome at a first location of a patient's skin, the method comprising: obtaining a first sub-epidermal moisture (SEM) value at the first location; obtaining a second SEM value at a second location of the patient's skin; and determining whether the difference between the first SEM value and the second SEM value exceeds a predetermined amount indicative of compartment syndrome.

BRIEF DESCRIPTION OF THE DRAWINGS

Aspects of the disclosure are herein described, by way of example only, with reference to the accompanying drawings.

With specific reference now to the drawings in detail, it is stressed that the particulars shown are by way of example and are for purposes of illustrative discussion of aspects of the disclosure. In this regard, the description and the drawings, considered alone and together, make apparent to those skilled in the art how aspects of the disclosure may be practiced.

FIG. 4A illustrates a first example of how the array of electrodes disclosed in FIG. 3 is configured to form a bioimpedance sensor according to the present disclosure.

FIG. 4B illustrates a second example of how the array of electrodes disclosed in FIG. 3 is configured to form a bioimpedance sensor according to the present disclosure.

DETAILED DESCRIPTION

Figure 1A:
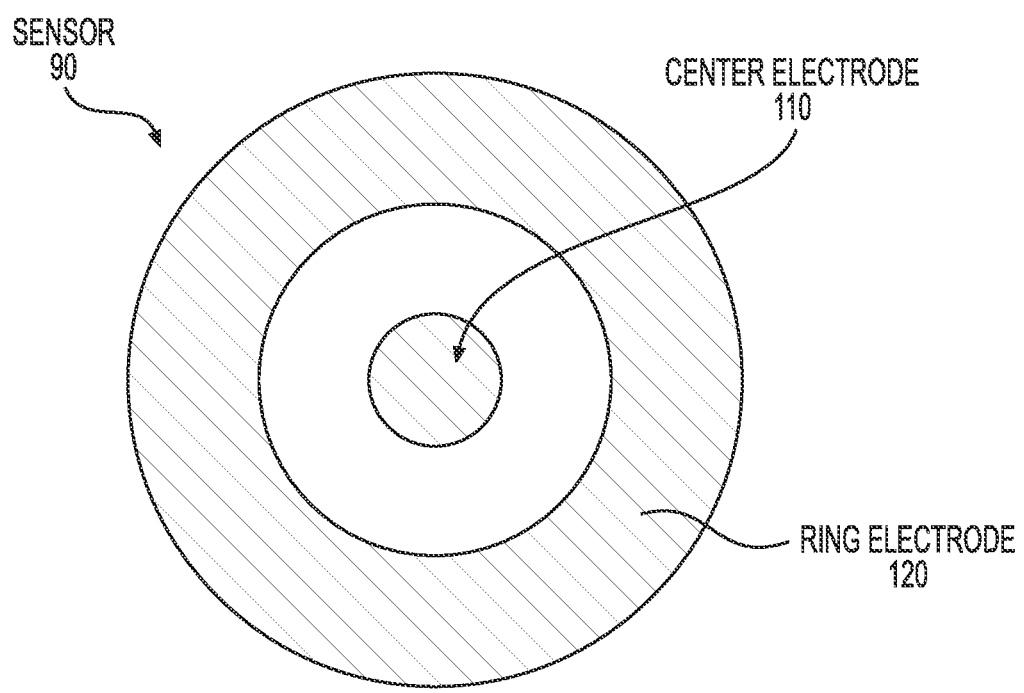
FIG. 1A discloses a toroidal bioimpedance sensor.

The present disclosure describes applications of the measurement of various electrical characteristics and derivation of SEM values to physical conditions and ailments associated with accumulation or depletion of extracellular fluid (ECF), also referred to as intercellular fluid. Examples provide application to particular conditions, including preeclampsia, dehydration, compartment syndrome, and burns and other open wounds. These examples are not limiting and the demonstrated principles may be applied to a larger scope of injuries and conditions than the specific example. For example, apparatus and methods disclosed in relation to a $3^{rd}$-degree burn may be used with equal efficacy to an open cut, gangrene, an ulcer, or other similar injury.

Women are susceptible to preeclampsia during pregnancy, with one of the symptoms being swelling in areas such as the face, hands, feet, or ankles. Providing a quantitative assessment of the degree of swelling would be beneficial compared to the subjective assessment methods current in use to assess the possibility of a patient having preeclampsia.

Patients who lose a significant amount of ECF are often considered to be dehydrated while, in fact, depletion of ECF is caused by hypovolemia, which is a decrease in volume of blood plasma. As intravascular volume is controlled by sodium regulation while the total body water content is not, it is important to differentiate between the two conditions so as to select the proper treatment.

Compartment syndrome occurs when excessive pressure builds up inside an enclosed muscle space in the body. Compartment syndrome may result from internal bleeding or swelling after an injury. The dangerously high pressure in compartment syndrome impedes the flow of blood to and from the affected tissues, which leads to tissue death if the blood flow is impeded for a sufficient amount of time. It can be an emergency, requiring surgery to prevent permanent injury and a quick and accurate assessment of this condition is vital to determining when to intervene.

This description is not intended to be a detailed catalog of all the different ways in which the disclosure may be implemented, or all the features that may be added to the instant disclosure. For example, features illustrated with respect to one embodiment may be incorporated into other embodiments, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to effect a disavowal of any part of the full scope of the invention. Hence, the following descriptions are intended to illustrate some particular embodiments of the disclosure, and not to exhaustively specify all permutations, combinations and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular aspects or embodiments only and is not intended to be limiting of the disclosure.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

U.S. patent application Ser. No. 14/827,375 discloses an apparatus that uses radio frequency (RF) energy to measure the sub-epidermal capacitance that corresponds to the moisture content of the target region of skin of a patient. The '375 application also discloses an array of these bipolar sensors of various sizes.

U.S. patent application Ser. No. 15/134,110 discloses an apparatus for measuring sub-epidermal moisture (SEM) using an RF signal at a frequency of 32 kHz to generate a bioimpedance signal, then converting this signal to a SEM value.

Both U.S. patent application Ser. Nos. 14/827,375 and 15/134,110 are incorporated herein by reference in their entireties.

Unless the context indicates otherwise, it is specifically intended that the various features of the disclosure described herein can be used in any combination. Moreover, the present disclosure also contemplates that in some aspects of the disclosure, any feature or combination of features set forth herein can be excluded or omitted.

The methods disclosed herein include and comprise one or more steps or actions for achieving the described method. The method steps and/or actions may be interchanged with one another without departing from the scope of the present invention. In other words, unless a specific order of steps or actions is required for proper operation of the embodiment, the order and/or use of specific steps and/or actions may be modified without departing from the scope of the present invention.

As used in the description of the disclosure and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a length, a frequency, or a SEM value and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, the term "sub-epidermal moisture" or "SEM" refers to the increase in tissue fluid and local edema caused by vascular leakiness and other changes that modify the underlying structure of the damaged tissue in the presence of continued pressure on tissue, apoptosis, necrosis, and the inflammatory process.

As used herein, a "system" may be a collection of devices in wired or wireless communication with each other.

As used herein, "interrogate" refers to the use of radiofrequency energy to penetrate into a patient's skin.

As used herein, a "patient" may be a human or animal subject.

As used herein, "total body water" or "TBW" refers to the total water content in a subject's body including intravascular fluid and extracellular fluid.

As used herein, "intravascular volume" refers to fluid contained within cells.

As used herein, "extracellular fluid" or "ECF" refers to bodily fluid contained outside of cells, including plasma, interstitial fluid, and transcellular fluid.

As used herein, "interstitial fluid" refers to fluid that surrounds tissue cells of a multicellular subject.

As used herein, "skin tent" refers to the slow return of the skin to its normal position after being pinched.

FIG. 1A discloses a toroidal bioimpedance sensor 90. In an aspect, a center electrode 110 is surrounded by a ring electrode 120. Without being limited to a particular theory, the gap between the two electrodes affects the depth of field penetration into the substrate below sensor 90. In one aspect, a ground plane (not visible in FIG. 1A, is parallel to and separate from the plane of the electrodes and, in an aspect, extends beyond the outer diameter of ring electrode 120. Without being limited to a particular theory, a ground plane may limit the field between electrodes 110 and 120 to a single side of the plane of the electrodes that is on the opposite side of the plane of the electrodes from the ground plane.

Figure 1B:
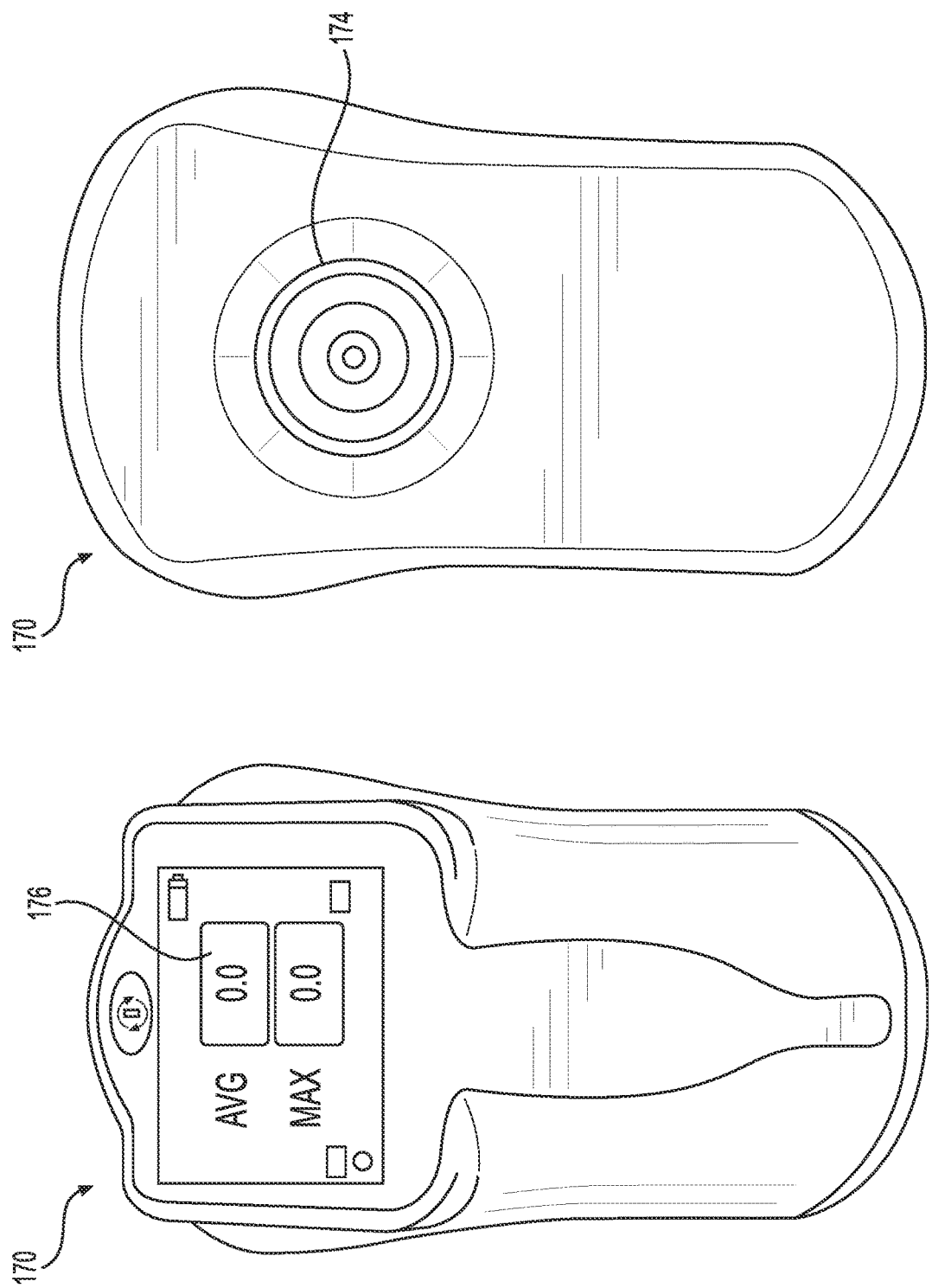
FIG. 1B discloses a SEM scanner that comprises the sensor of FIG. 1A.

FIG. 1B provides top and bottom views of a SEM scanner 170 that comprise electronics that drive sensor 174, which is similar to sensor 90 of FIG. 1, and measure a capacitance between electrodes 110 and 120. This capacitance is converted to a SEM value that is displayed on display 176.

Aspects of sensor 90 and SEM scanner 170 are disclosed in International Publication No. WO 2016/172263, from which the U.S. patent application Ser. No. 15/134,110 was filed as a national phase entry, all of which are hereby incorporated by reference in their entireties.

Figure 2:
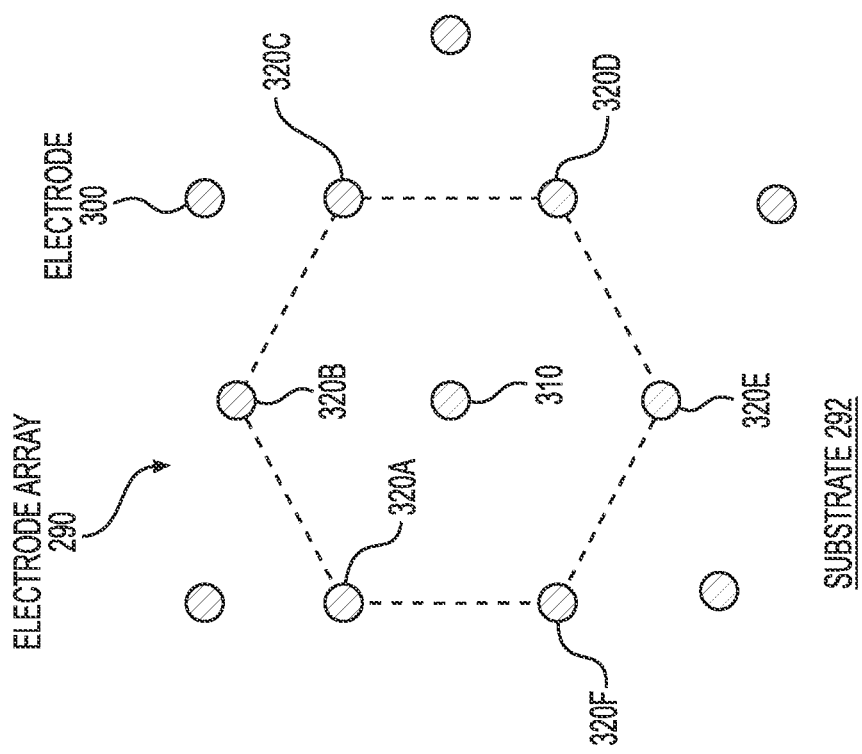
FIG. 2 is a first exemplary array of electrodes.

FIG. 2 depicts an exemplary electrode array 290, according to the present disclosure. Array 290 is composed of individual electrodes 300 disposed, in this example, in a regular pattern over a substrate 292. In an aspect, each electrode 300 is separately coupled (through conductive elements not shown in FIGS. 6 through 8B) to a circuit, such as described with respect to FIG. 4A, that is configured to measure an electrical parameter. In one aspect, a "virtual sensor" is created by selective connection of predetermined subsets of electrodes 300 to a common element of a circuit. In this example, a particular electrode 310 is connected as a center electrode, similar to electrode 110 of FIG. 1A, and six electrodes 320A-320F are connected together as a "virtual ring" electrode, similar to electrode 120 of FIG. 1A. In an aspect, two individual electrodes are individually connected to a circuit to form a virtual sensor, for example electrodes 310 and 320A are respectively connected as two electrodes of a sensor. In one aspect, one or more electrodes 300 are connected together to form one or the other of the electrodes of a two-electrode sensor.

Any pair of electrodes, whether composed of single electrodes or a set of electrodes coupled together to form virtual electrodes, is coupled to electronics that are configured to measure an electrical property or parameter that comprises one or more of electrical characteristics selected from the group consisting of a resistance, a capacitance, an inductance, an impedance, a reluctance, or other electrical characteristic with one or more of sensors 90, 174, 290, 430, 440, or other two-electrode sensor.

Figure 3:
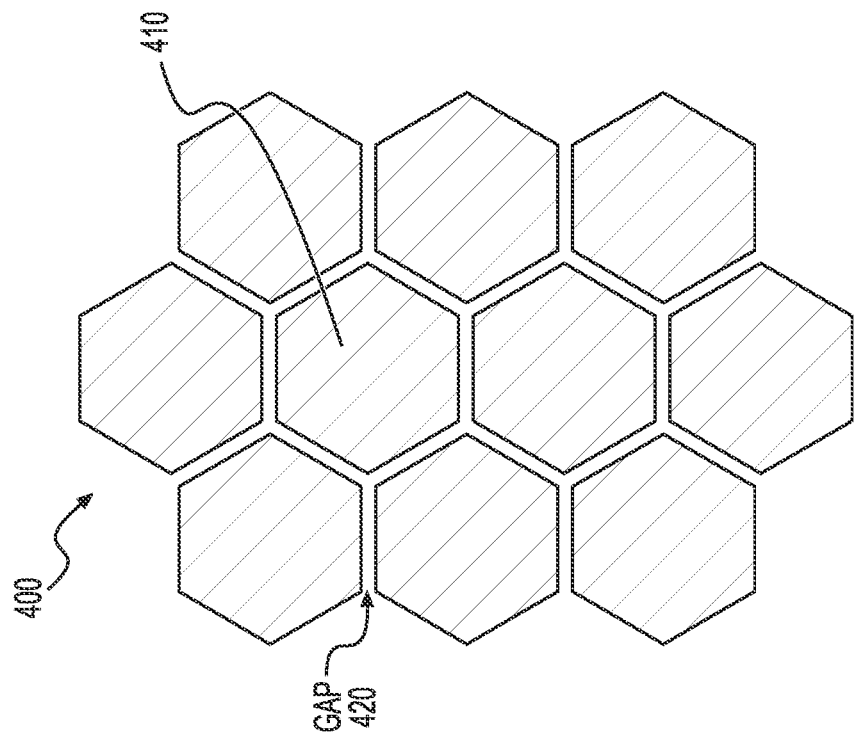
FIG. 3 is an exemplary array of electrodes according to the present disclosure.

FIG. 3 depicts another exemplary array 400 of electrodes 410, according to the present disclosure. In this example, each of electrodes 410 is an approximate hexagon that is separated from each of the surrounding electrodes 410 by a gap 420. In an aspect, electrodes 410 are one of circles, squares, pentagons, or other regular or irregular shapes. In one aspect, gap 420 is uniform between all electrodes 410. In an aspect, gap 420 varies between various electrodes. In one aspect, gap 420 has a width that is narrower than the cross-section of each of electrodes 410. Electrodes 410 may be interconnected to form virtual sensors as described below with respect to FIGS. 8A and 8B.

FIG. 4A depicts an array 400 of electrodes 410 that are configured, e.g. connected to a measurement circuit, to form an exemplary sensor 430, according to the present disclosure. A single hexagonal electrode 410 that is labeled with a "1" forms a center electrode and a ring of electrodes 410 that are marked with a "2" are interconnected to form a ring electrode. In one aspect, electrodes 410 between the center and ring electrode are electrically "floating." In an aspect, electrodes 410 between the center and ring electrode are grounded or connected to a floating ground. In one aspect, electrodes 410 that are outside the ring electrode are electrically "floating." In an aspect, electrodes 410 that are outside the virtual ring electrode are grounded or connected to a floating ground.

FIG. 4B depicts an alternate aspect where array 400 of electrodes 410 has been configured to form a virtual sensor 440, according to the present disclosure. In an aspect, multiple electrodes 410, indicated by a "1," are interconnected to form a center electrode while a double-wide ring of electrodes, indicated by a "2," are interconnected to form a ring electrode. In one aspect, various numbers and positions of electrodes 410 are interconnected to form virtual electrodes of a variety of sizes and shapes.

Figure 5A:
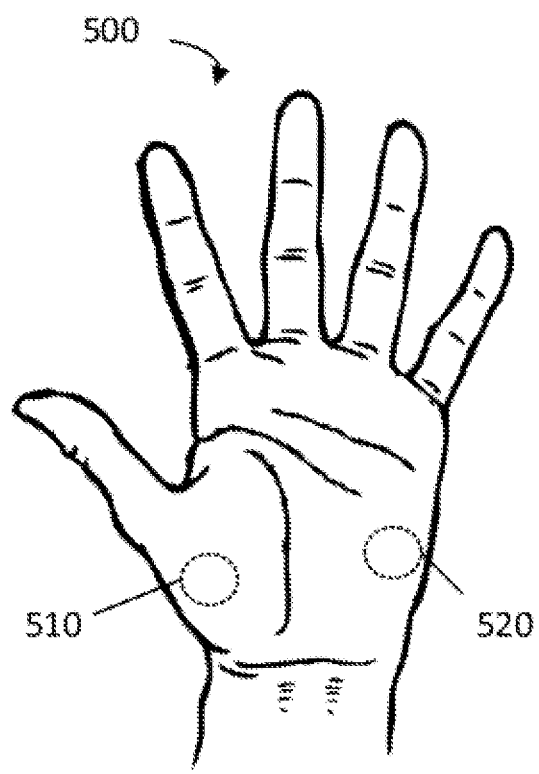
FIG. 5A illustrates exemplary measurement locations for assessment of edema related to preeclampsia on a hand according to the present disclosure.

FIG. 5A discloses exemplary measurement locations 510 and 520 on a hand 500 for assessment of edema related to preeclampsia, according to the present disclosure. Location 510 is generally located on the thenar of a left hand, while location 520 is generally located on the hypothenar eminence of a left hand. Similar locations exist in the same areas of a right hand. Other locations where edema related to preeclampsia is observable are known to those in the field. In an aspect, a measured SEM value may be compared to a predetermined reference value, where the measured SEM value being above or below a threshold is indicative of edema. In one aspect, multiple measurements taken at multiple locations are averaged or compared to an average, where a difference between a reading and the average is indicative of edema at the respective location. In an aspect, a maximum and a minimum SEM value are identified within a set of measurements, where a characteristic of the comparison such as the difference between the maximum and minimum is compared to a predetermined threshold. In one aspect, a SEM value measured at a first predetermined location is compared to a SEM value measured at a second predetermined location, where a characteristic of the comparison such as a difference greater than a threshold is indicative of edema at one of the locations.

Figure 5C:
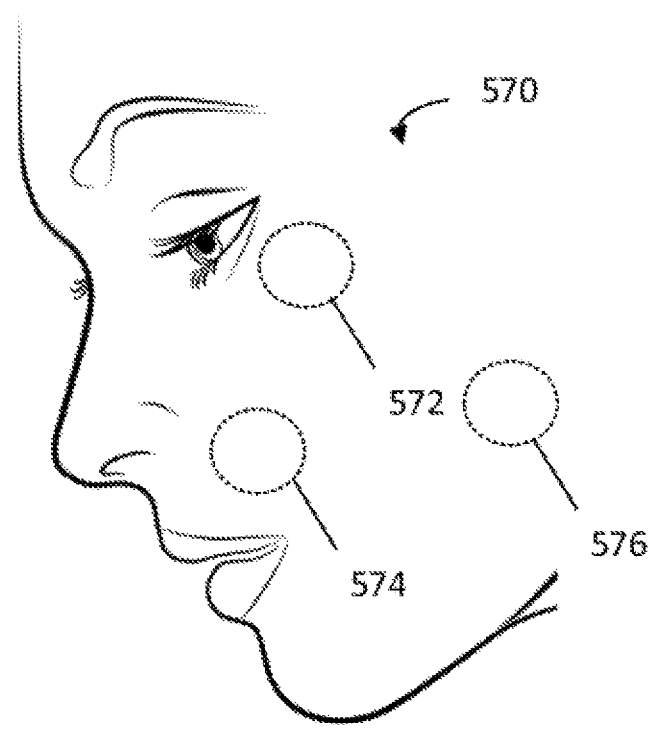
FIG. 5C illustrates exemplary measurement locations for assessment of edema related to preeclampsia on the face according to the present disclosure.
Figure 5B:
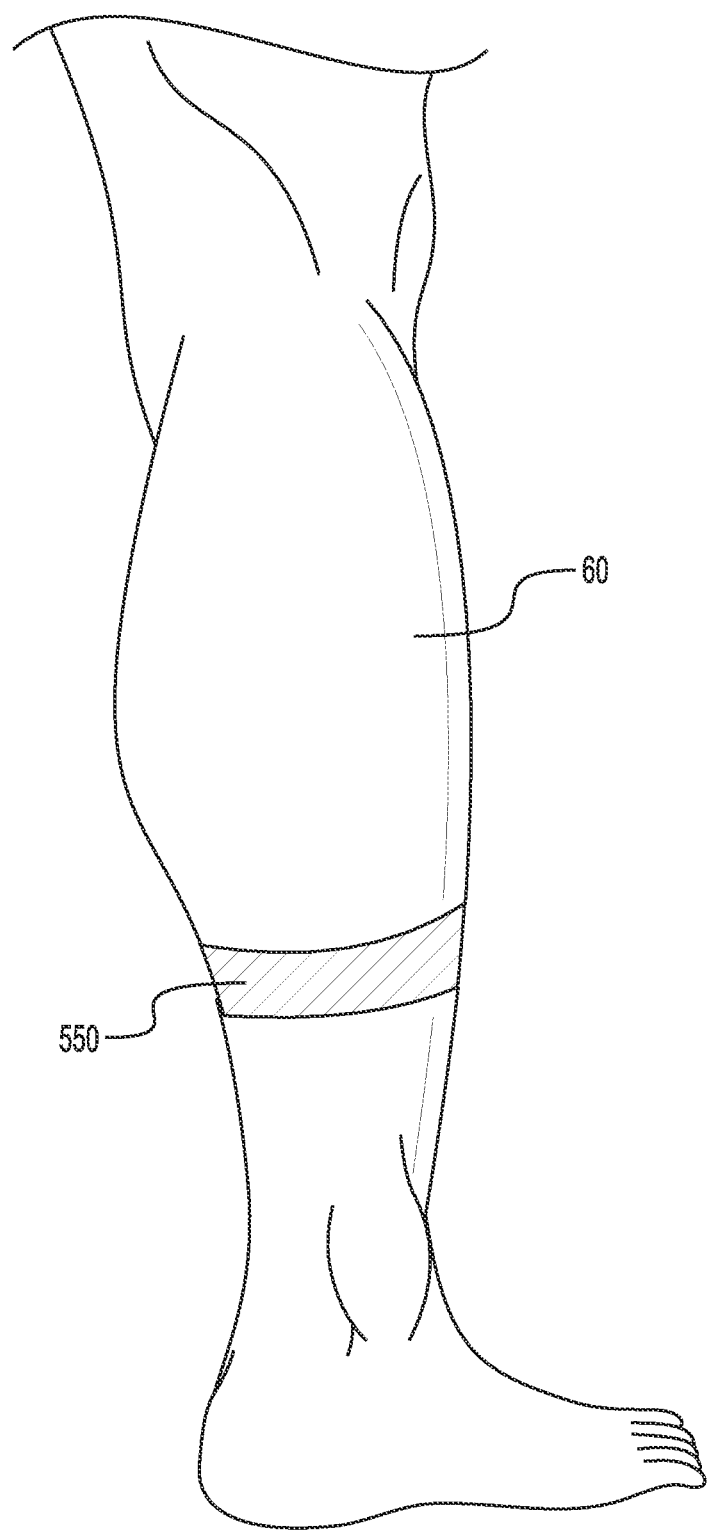
FIG. 5B illustrates exemplary measurement locations for assessment of edema related to preeclampsia at the upper ankle region according to the present disclosure.

FIG. 5B disclose exemplary measurement locations 552 and 562 for assessment of edema in upper ankle region 550 and foot 560 that are related to preeclampsia, according to the present disclosure. In an aspect, SEM values derived from measurements made at one of more locations 552 and 562 are compared to each other, a parameter calculated from one of more of the measurements, e.g. an average SEM value, or to predetermined thresholds.

In one aspect, a SEM sensor as described herein, for example sensor 90 or sensor 400, is embedded in a band 554 that can be wrapped around a calf as shown in FIG. 5B. In one aspect, band 554 comprises sensors configured to measure one or more of oxygenation of the tissue, which may comprise measurement of one or both of oxyhemoglobin and deoxyhemoglobin, temperature of one or more points on the skin, pulse rate, and blood pressure in a patient. In an aspect, the combination of measurements made by band 554 provides information regarding blood flow and edema in the lower leg of a patient.

FIG. 5C discloses exemplary measurement locations 572, 574, 576 for assessment of edema on face 570 that is related to preeclampsia, according to the present disclosure. Swelling may occur in one or more of location 572 near the eyes, location 574 on the infraorbital triangle, location 574 over the cheek bone, or other locations between and around locations in a patient as identified in FIG. 5C. SEM values derived from measurements at one of more of these locations may be assessed as discussed in relation to FIGS. 5A and 5B.

In general, edema caused by preeclampsia is a system condition and would be expected to be present at the same level in equivalent locations on a patient's body. For example, swelling of a left hand would be expected to be roughly the same as the corresponding right hand, and vice versa. In one aspect, a SEM scanner comprises two electrodes, a circuit electronically coupled to the electrodes and configured to measure an electrical property between the electrodes and provide information regarding the electrical property to a processor that is configured to convert the information into a SEM value. In an aspect, multiple electrical property measurements are used to generate an average SEM value. A processor of a SEM scanner then compares SEM values derived from measurements at similar locations and calculated one or more of an average, a difference, a percentage difference, or other computational characteristic of the set of SEM values. In an aspect, a determination that the SEM values in two corresponding locations are both above a predetermined threshold and are also within a predetermined range of each other is indicative of preeclampsia. In one aspect, a single SEM value exceeding a reference value, which may be predetermined or derived from other SEM measurements, is indicative of preeclampsia.

In an aspect, a predetermined reference value for preeclampsia may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a predetermined reference value for preeclampsia may range from 0.1 to 4.0, such as from 0.5 to 4.0, from 0.1 to 3.5, from 1.0 to 3.5, from 1.5 to 4.0, from 1.5 to 3.5, from 2.0 to 4.0, from 2.5 to 3.5, from 2.0 to 3.0, from 2.0 to 2.5, or from 2.5 to 3.0. In one aspect, a predetermined reference value for preeclampsia may range from 4.1 to 8.0, such as from 4.5 to 8.0, from 4.1 to 7.5, from 5.0 to 7.5, from 5.5 to 7.0, from 5.5 to 7.5, from 6.0 to 8.0, from 6.5 to 7.5, from 6.0 to 7.0, from 6.0 to 6.5, or from 6.5 to 7.0. In one aspect, a predetermined reference value for preeclampsia may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In an aspect, a predetermined reference value for preeclampsia can be scaled by a factor or a multiple based on the values provided herein.

One or more regions may be defined on a body. In an aspect, measurements made within a region are considered comparable to each other. A region may be defined as an area on the skin of the body wherein measurements may be taken at any point within the area. In an aspect, a region corresponds to an anatomical region (e.g., heel, ankle, lower back). In an aspect, a region may be defined as a set of two or more specific points relative to anatomical features wherein measurements are taken only at the specific points. In an aspect, a region may comprise a plurality of non-contiguous areas on the body. In an aspect, the set of specific locations may include points in multiple non-contiguous areas.

In an aspect, a region is defined by surface area. In an aspect, a region may be, for example, between 5 and 200 $cm^2$, between 5 and 100 $cm^2$, between 5 and 50 $cm^2$, or between 10 and 50 $cm^2$, between 10 and 25 $cm^2$, or between 5 and 25 $cm^2$.

In an aspect, measurements may be made in a specific pattern or portion thereof. In an aspect, the pattern of readings is made in a pattern with the target area of concern in the center. In an aspect, measurements are made in one or more circular patterns of increasing or decreasing size, T-shaped patterns, a set of specific locations, or randomly across a tissue or region. In an aspect, a pattern may be located on the body by defining a first measurement location of the pattern with respect to an anatomical feature with the remaining measurement locations of the pattern defined as offsets from the first measurement position.

In an aspect, a plurality of measurements are taken across a tissue or region and the difference between the lowest measurement value and the highest measurement value of the plurality of measurements is recorded as a delta value of that plurality of measurements. In an aspect, 3 or more, 4 or more, 5 or more, 6 or more, 7 or more, 8 or more, 9 or more, or 10 or more measurements are taken across a tissue or region.

In an aspect, a threshold may be established for at least one region. In an aspect, a threshold of 0.2, 0.3, 0.4, 0.5, 0.6, 0.7, 0.8, 0.9, or other value may be established for the at least one region. In an aspect, a delta value is identified as significant when the delta value of a plurality of measurements taken within a region meets or exceeds a threshold associated with that region. In an aspect, each of a plurality of regions has a different threshold. In an aspect, two or more regions may have a common threshold.

In an aspect, a threshold has both a delta value component and a chronological component, wherein a delta value is identified as significant when the delta value is greater than a predetermined numerical value for a predetermined portion of a time interval. In an aspect, the predetermined portion of a time interval is defined as a minimum of X days wherein a plurality of measurements taken that day produces a delta value greater than or equal to the predetermined numerical value within a total of Y contiguous days of measurement. In an aspect, the predetermined portion of a time interval may be defined as 1, 2, 3, 4, or 5 consecutive days on which a plurality of measurements taken that day produces a delta value that is greater than or equal to the predetermined numerical value. In an aspect, the predetermined portion of a time interval may be defined as some portion of a different specific time period (weeks, month, hours etc.).

In an aspect, a threshold has a trending aspect wherein changes in the delta values of consecutive pluralities of measurements are compared to each other. In an aspect, a trending threshold is defined as a predetermined change in delta value over a predetermined length of time, wherein a determination that the threshold has been met or exceeded is significant. In an aspect, a determination of significance will cause an alert to be issued. In an aspect, a trend line may be computed from a portion of the individual measurements of the consecutive pluralities of measurements. In an aspect, a trend line may be computed from a portion of the delta values of the consecutive pluralities of measurements.

In an aspect, the number of measurements taken within a single region may be less than the number of measurement locations defined in a pattern. In an aspect, a delta value will be calculated after a predetermined initial number of readings, which is less than the number of measurement locations defined in a pattern, have been taken in a region and after each additional reading in the same region, wherein additional readings are not taken once the delta value meets or exceeds the threshold associated with that region.

In an aspect, the number of measurements taken within a single region may exceed the number of measurement locations defined in a pattern. In an aspect, a delta value will be calculated after each additional reading.

In an aspect, a quality metric may be generated for each plurality of measurements. In an aspect, this quality metric is chosen to assess the repeatability of the measurements. In an aspect, this quality metric is chosen to assess the skill of the clinician that took the measurements. In an aspect, the quality metric may include one or more statistical parameters, for example an average, a mean, or a standard deviation. In an aspect, the quality metric may include one or more of a comparison of individual measurements to a predefined range. In an aspect, the quality metric may include comparison of the individual measurements to a pattern of values, for example comparison of the measurement values at predefined locations to ranges associated with each predefined location. In an aspect, the quality metric may include determination of which measurements are made over healthy tissue and one or more evaluations of consistency within this subset of "healthy" measurements, for example a range, a standard deviation, or other parameter.

In one aspect, a measurement, for example, a threshold value, is determined by SEM Scanner Model 200 (Bruin Biometrics, LLC, Los Angeles, Calif.). In another aspect, a measurement is determined by another SEM scanner.

In an aspect, a measurement value is based on a capacitance measurement by reference to a reference device. In an aspect, a capacitance measurement can depend on the location and other aspects of any electrode in a device. Such variations can be compared to a reference SEM device such as an SEM Scanner Model 200 (Bruin Biometrics, LLC, Los Angeles, Calif.). A person of ordinary skill in the art understands that the measurements set forth herein can be adjusted to accommodate a difference capacitance range by reference to a reference device.

Figure 6:
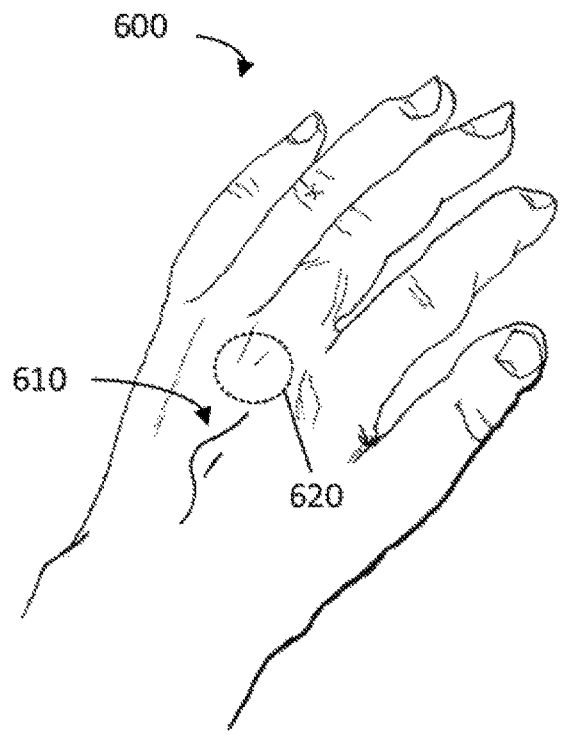
FIG. 6 discloses an exemplary measurement location for assessment of dehydration on the back of a hand according to the present disclosure.

FIG. 6 discloses an exemplary measurement location for assessment of dehydration, according to the present disclosure. Dehydration is often used to describe either true dehydration, which is a reduction in the total body water, or as a proxy for hypovolemia, which is a decrease in volume of blood plasma. Total body water is not controlled via sodium regulation while intravascular volume is controlled by sodium regulation, so this distinction is important to guide therapy. Patients who lose a significant amount of ECF are often considered to be dehydrated while, in fact, depletion of ECF is caused by hypovolemia. Providing accurate guidance as to the amount of interstitial, or extracellular, fluid is therefore important guidance to a clinician treating the patient.

A current method of assessing hydration is to pull up a skin tent 610 in an area of loose skin and assess how skin tent 610 relaxes, where a slow return or failure to completely return is considered indicative of dehydration.

Measuring capacitance, or other electrical characteristic of the local tissue of a patient, using sensors such as sensor 90 or 440, will detect a reduction in the amount of ECF. An exemplary location for assessment of dehydration is location 620 over the junction of the second and third compartment of a hand. Comparison of SEM values derived from such measurements with predetermined thresholds will provide a quantitative indication of whether a patient is suffering from hypovolemia. In an aspect, use of a SEM measurement to assess the amount of ECF in conjunction with a measurement that is responsive to the total water content of a tissue, which includes both the ECF and the fluid within cells, and comparison of the two measurements with thresholds or with each other will provide an indication of true dehydration. In an aspect, multiple electrical property measurements are used to generate an average SEM value to assess the amount of ECF. In an aspect, a single SEM value being less than a reference value, which may be predetermined or derived from other SEM measurements, is indicative of hypovolemia.

In an aspect, a predetermined reference value for hypovolemia may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a predetermined reference value for hypovolemia may range from 0.1 to 4.0, such as from 0.5 to 4.0, from 0.1 to 3.5, from 1.0 to 3.5, from 1.5 to 4.0, from 1.5 to 3.5, from 2.0 to 4.0, from 2.5 to 3.5, from 2.0 to 3.0, from 2.0 to 2.5, or from 2.5 to 3.0. In one aspect, a predetermined reference value for hypovolemia may range from 4.1 to 8.0, such as from 4.5 to 8.0, from 4.1 to 7.5, from 5.0 to 7.5, from 5.5 to 7.0, from 5.5 to 7.5, from 6.0 to 8.0, from 6.5 to 7.5, from 6.0 to 7.0, from 6.0 to 6.5, or from 6.5 to 7.0. In one aspect, a predetermined reference value for hypovolemia may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In an aspect, a predetermined reference value for hypovolemia can be scaled by a factor or a multiple based on the values provided herein.

Figure 7A:
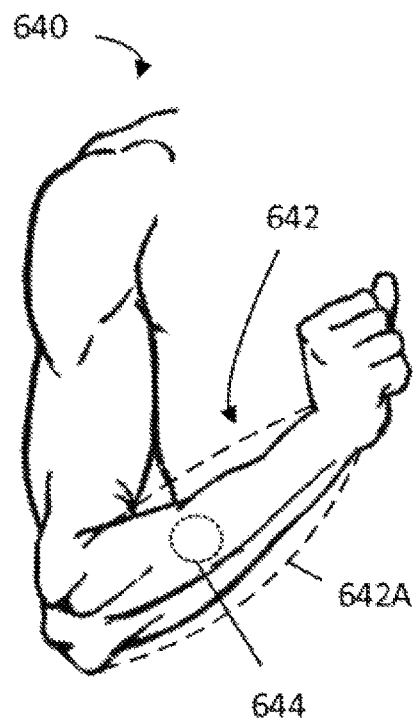
FIG. 7A illustrates an exemplary measurement location for assessment of compartment syndrome in the forearm area according to the present disclosure.
Figure 7B:
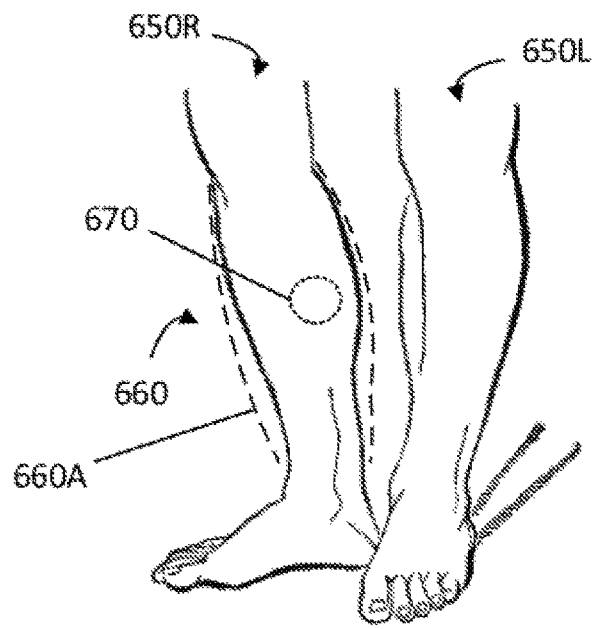
FIG. 7B illustrates an exemplary measurement location for assessment of compartment syndrome in the calf area according to the present disclosure.

FIGS. 7A and 7B disclose exemplary measurement locations for assessment of compartment syndrome, according to the present disclosure. Compartment syndrome is defined as a symptom complex resulting from increased tissue pressure within a limited space that compromises the circulation and function of the contents of that space. This occurs when intramuscular pressure is elevated to a level and for a period of time sufficient to reduce capillary perfusion. Muscles and nerves can tolerate ischemia up to 4 hours and irreversible damage occurs at 8 hours. There are numerous compartments in a human body, including three forearm compartments and ten separate osteofascial compartments in the hand. Symptoms of compartment syndrome include pain in the affected region, passive stretching of the involved muscles, localized swelling, paresthesia (e.g. tingling) in the involved nerve distribution, and muscle paresis (e.g. weakness). Current practice for quantification of the degree of compartment syndrome for a limb is to measure the circumference of the limb at sequential times. This method is slow and dependent upon the time period between the injury and the initial measurement. A new method to quantify edema within a compartment and to track changes in the degree of edema on a time scale of minutes would provide important information to a clinician.

The swelling of compartment syndrome is thought to be driven primarily by ECF. Measurement of the capacitance of tissue in a compartment will respond to the increase in ECF. As compartment syndrome typically affects only one region of the body, for example a single leg, SEM values can be derived from capacitance measurements on corresponding locations on both the affected leg and the other leg and compared, with a difference greater than a predetermined threshold being indicative of compartment syndrome. In one aspect, the magnitude of the difference between measurements of an affected and an unaffected body part is indicative of the severity of compartment syndrome and the associated urgency of the condition.

In an aspect, a predetermined threshold indicative of compartment syndrome may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a predetermined threshold indicative of compartment syndrome may range from 0.1 to 4.0, such as from 0.5 to 4.0, from 0.1 to 3.5, from 1.0 to 3.5, from 1.5 to 4.0, from 1.5 to 3.5, from 2.0 to 4.0, from 2.5 to 3.5, from 2.0 to 3.0, from 2.0 to 2.5, or from 2.5 to 3.0. In one aspect, a predetermined threshold indicative of compartment syndrome may range from 4.1 to 8.0, such as from 4.5 to 8.0, from 4.1 to 7.5, from 5.0 to 7.5, from 5.5 to 7.0, from 5.5 to 7.5, from 6.0 to 8.0, from 6.5 to 7.5, from 6.0 to 7.0, from 6.0 to 6.5, or from 6.5 to 7.0. In one aspect, a predetermined threshold indicative of compartment syndrome may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In an aspect, a predetermined threshold indicative of compartment syndrome can be scaled by a factor or a multiple based on the values provided herein.

In FIG. 7A, forearm 642 of arm 640 is swelling as schematically indicated by dashed line envelope 642A. A measurement in a location 644 that is selected to be directly coupled to one of the compartments in forearm 642 will provide a SEM value that is related to the degree of edema in that compartment. Comparison of this SEM value with a second SEM value derived from a measurement in an equivalent location (not shown in FIG. 7A) on the other arm will provide information on the degree of edema and the severity of the condition. In an aspect, s SEM value is associated with a pressure in the measured compartment.

FIG. 7B depicts a situation for a right leg 650R that is similar to the situation of FIG. 7A. Lower leg 660 is swelling as indicated by dashed line envelope 660A. An SEM value derived from a capacitance measurement at location 670, which has been selected to be coupled to one of the compartments in lower leg 650R, will provide an indication of the edema in that compartment. As in FIG. 7A, an SEM value from a corresponding location (not shown in FIG. 7B) on left lower leg 650L provides a baseline, where a comparison of the two readings provides an indication of the degree of edema and urgency of the compartment syndrome.

From the foregoing, it will be appreciated that the present invention can be embodied in various ways, which include but are not limited to the following:

Embodiment 1

An apparatus for assessing preeclampsia, the apparatus comprising: a sensor comprising at least one first electrode and at least one second electrode, where the sensor is configured to be placed against a patient's skin, a circuit electronically coupled to the first and second electrodes and configured to measure an electrical property between the first and second electrodes and provide information regarding the electrical property, a processor electronically coupled to the circuit, and a non-transitory computer-readable medium electronically coupled to the processor and comprising instructions stored thereon that, when executed on the processor, perform the steps of: receiving information from the circuit, converting the information into a first sub-epidermal moisture (SEM) value, and determining a difference between the first SEM value and a reference value, where the magnitude of the difference exceeding the reference value is indicative of preeclampsia.

Embodiment 2

The apparatus of embodiment 1, where the reference value is predetermined.

Embodiment 3

An apparatus for assessing hypovolemia, the apparatus comprising: a sensor comprising at least one first electrode and at least one second electrode, where the sensor is configured to be placed against a patient's skin, a circuit electronically coupled to the first and second electrodes and configured to measure an electrical property between the first and second electrodes and provide information regarding the electrical property, a processor electronically coupled to the circuit, and a non-transitory computer-readable medium electronically coupled to the processor and comprising instructions stored thereon that, when executed on the processor, perform the steps of: receiving information from the circuit, converting the information into a first sub-epidermal moisture (SEM) value, and determining a difference between the first SEM value and a reference value, where the magnitude of the difference lesser than the reference value is indicative of hypovolemia.

Embodiment 4

The apparatus of embodiment 3, where the reference value is predetermined.

Embodiment 5

A method for detecting preeclampsia at a first location of a patient's skin, the method comprising: obtaining a sub-epidermal moisture (SEM) value at the first location; and determining that the SEM value is greater than a reference value to indicate preeclampsia.

Embodiment 6

The method of embodiment 5, where the reference value is predetermined.

Embodiment 7

A method for detecting hypovolemia at a first location of a patient's skin, the method comprising: obtaining a sub-epidermal moisture (SEM) value at the first location; and determining that the SEM value is lesser than a reference value to indicate hypovolemia.

Embodiment 8

The method of embodiment 7, where the reference value is predetermined.

Embodiment 9

An apparatus for assessing compartment syndrome, the apparatus comprising: a sensor comprising at least one first electrode and at least one second electrode, where the sensor is configured to be placed against a patient's skin, a circuit electronically coupled to the first and second electrodes and configured to measure an electrical property between the first and second electrodes and provide information regarding the electrical property, a processor electronically coupled to the circuit, and a non-transitory computer-readable medium electronically coupled to the processor and comprising instructions stored thereon that, when executed on the processor, perform the steps of: receiving information from the circuit, converting the information into a first sub-epidermal moisture (SEM) value, and determining a difference between the first SEM value and a reference value, where the magnitude of the difference exceeding a predetermined amount is indicative of compartment syndrome.

Embodiment 10

The apparatus of embodiment 9, where: the first SEM value is derived from a measurement taken at a first location of the patient's skin; the reference value is a second SEM value derived from a measurement taken at a second location of the patient's skin.

Embodiment 11

The apparatus of embodiment 10, where the first and second locations are symmetric with respect to a centerline of the patient's body.

Embodiment 12

The apparatus of embodiment 10, where the first SEM value exceeding the second SEM value by the predetermined amount is indicative of compartment syndrome at the first location.

Embodiment 13

The apparatus of embodiment 10, where the second SEM value exceeding the first SEM value by the predetermined amount is indicative of compartment syndrome at the second location.

Embodiment 14

A method for detecting compartment syndrome at a first location of a patient's skin, the method comprising: obtaining a first sub-epidermal moisture (SEM) value at the first location; obtaining a second SEM value at a second location of the patient's skin; and determining whether the difference between the first SEM value and the second SEM value exceeds a predetermined amount indicative of compartment syndrome.

Embodiment 15

The method of embodiment 14, where the first and second locations are symmetric with respect to a centerline of the patient's body.

Embodiment 16

The method of embodiment 14, where the first SEM value exceeding the second SEM value by the predetermined amount is indicative of compartment syndrome at the first location.

Embodiment 17

The method of embodiment 14, where the second SEM value exceeding the first SEM value by the predetermined amount is indicative of compartment syndrome at the second location.

While the invention has been described with reference to particular aspects, it will be understood by those skilled in the art that various changes may be made and equivalents may be substituted for elements thereof without departing from the scope of the invention. In addition, many modifications may be made to a particular situation or material to the teachings of the invention without departing from the scope of the invention. Therefore, it is intended that the invention not be limited to the particular aspects disclosed but that the invention will include all aspects falling within the scope and spirit of the appended claims.

We claim:

1. An apparatus for assessing preeclampsia, said apparatus comprising:
   a sensor comprising at least one first electrode and at least one second electrode, wherein said sensor is configured to be placed against a patient's skin sequentially at a first location and a second location, wherein the locations are corresponding locations on a patient's body,
   a circuit electronically coupled to said first and second electrodes and configured to measure a first electrical property and a second electrical property at said first and said second locations respectively and provide information regarding said first and said second electrical properties, wherein each electrical property is measured between said first and second electrodes,
   a processor electronically coupled to said circuit and configured to receive said information, and
   a non-transitory computer-readable medium electronically coupled to said processor and comprising instructions stored thereon that, when executed on said processor, perform the steps of:
   converting said information regarding said first and second electrical properties into a first sub-epidermal moisture (SEM) value and a second SEM value, respectively, and
   comparing said first SEM value and said second SEM value to a predetermined threshold,
   wherein a determination that said first SEM value and said second SEM value are both above the predetermined threshold and are also within a predetermined range of each other indicates preeclampsia in said patient.

2. An apparatus for assessing compartment syndrome, said apparatus comprising:
   a sensor comprising at least one first electrode and at least one second electrode, wherein said sensor is configured to be placed against a patient's skin,
   a circuit electronically coupled to said first and second electrodes and configured to measure an electrical property between said first and second electrodes and provide information regarding said electrical property,
   a processor electronically coupled to said circuit and configured to receive said information, and
   a non-transitory computer-readable medium electronically coupled to said processor and comprising instructions stored thereon that, when executed on said processor, perform the steps of:
   converting said information into a first sub-epidermal moisture (SEM) value, and
   determining a difference between said first SEM value and a reference value,
   wherein said first SEM value is derived from a measurement taken at a first location of the patient's skin, wherein said first SEM value corresponds to a level of extracellular fluid (ECF) at said first location of the patient's skin,
   wherein said reference value is a second SEM value derived from a measurement taken at a second location of the patient's skin, wherein said second SEM value corresponds to a level of ECF at said second location of the patient's skin,
   wherein said first location is located in a first compartment of the patient's body and said second location is located in a second compartment of the patient's body, and
   wherein the magnitude of the difference exceeding a predetermined amount is indicative of compartment syndrome.

3. The apparatus of claim 2, wherein said first and second locations are symmetric with respect to a centerline of the patient's body.

4. The apparatus of claim 2, wherein said first SEM value exceeding said second SEM value by said predetermined amount is indicative of compartment syndrome at said first location.

5. The apparatus of claim 2, wherein said second SEM value exceeding said first SEM value by said predetermined amount is indicative of compartment syndrome at said second location.

6. The apparatus of claim 2, wherein the first compartment is a forearm compartment in one arm and the second compartment is the corresponding forearm compartment in the other arm.

7. The apparatus of claim 2, wherein the first compartment is a calf compartment in one leg and the second compartment is the corresponding calf compartment in the other leg.

8. The apparatus of claim 2, wherein the first compartment is an osteofascial compartment in one hand and the second compartment is the corresponding osteofascial compartment in the other hand.

* * * * *